(12) United States Patent
Garber et al.

(10) Patent No.: US 7,429,645 B2
(45) Date of Patent: Sep. 30, 2008

(54) HUMANIZED ANTI-LYMPHOTOXIN BETA RECEPTOR ANTIBODIES

(75) Inventors: Ellen Garber, Cambridge, MA (US); Kenneth Simon, Cambridge, MA (US); Jose William Saldanha, Enfield (GB)

(73) Assignee: Biogen Idec MA Inc., Cambridge, MA (US)

( * ) Notice: Subject to any disclaimer, the term of this patent is extended or adjusted under 35 U.S.C. 154(b) by 124 days.

(21) Appl. No.: 11/021,819

(22) Filed: Dec. 23, 2004

(65) Prior Publication Data

US 2006/0222644 A1 Oct. 5, 2006

Related U.S. Application Data

(63) Continuation of application No. PCT/US03/20762, filed on Jul. 1, 2003.

(60) Provisional application No. 60/392,993, filed on Jul. 1, 2002, provisional application No. 60/417,372, filed on Oct. 9, 2002.

(51) Int. Cl.
*C12P 21/08* (2006.01)
*C07K 16/00* (2006.01)
*A61K 39/395* (2006.01)
*C12P 21/04* (2006.01)
*C07H 21/04* (2006.01)

(52) U.S. Cl. ............ 530/387.3; 530/388.1; 530/388.22; 530/391.7; 424/133.1; 424/141.1; 424/143.1; 424/181.1; 435/69.6; 435/70.21

(58) Field of Classification Search ...................... None
See application file for complete search history.

(56) References Cited

U.S. PATENT DOCUMENTS

| | | | |
|---|---|---|---|
| 5,530,101 A | | 6/1996 | Queen et al. |
| 5,618,920 A | * | 4/1997 | Robinson et al. |
| 5,859,205 A | * | 1/1999 | Adair et al. |
| 5,925,351 A | | 7/1999 | Browning et al. |
| 6,312,691 B1 | * | 11/2001 | Browning et al. |
| 6,403,087 B1 | | 6/2002 | Browning et al. |
| 6,669,941 B1 | | 12/2003 | Browning et al. |
| 7,001,598 B2 | | 2/2006 | Browning et al. |
| 7,060,667 B1 | | 6/2006 | Browning et al. |
| 2004/0058394 A1 | | 3/2004 | Garber et al. |
| 2005/0037003 A1 | | 2/2005 | Browning et al. |
| 2005/0281811 A1 | | 12/2005 | Browning et al. |
| 2006/0104971 A1 | | 5/2006 | Garber et al. |
| 2006/0134102 A1 | | 6/2006 | LePage et al. |
| 2006/0280722 A1 | | 12/2006 | Browning et al. |
| 2007/0154476 A1 | | 7/2007 | Browning et al. |

FOREIGN PATENT DOCUMENTS

| | | |
|---|---|---|
| EP | 0519596 B1 | 12/1992 |
| WO | WO-91/09967 A1 | 7/1991 |
| WO | WO-92/00329 A1 | 1/1992 |
| WO | WO-94/04679 A1 | 3/1994 |
| WO | WO-94/13808 A2 | 6/1994 |
| WO | WO 9622788 A1 * | 8/1996 |
| WO | WO-99/38525 A1 | 8/1999 |
| WO | WO 9958679 A1 * | 11/1999 |

OTHER PUBLICATIONS

Campbell et al. Biology, 5th ed. p. 856, 1999.*
Co et al. Nature, 351(6):501-502, Jun. 6, 1991.*
William E. Paul, Fundamental immunology, 3rd ed., p. 242, 292-295, 1993.*
Rudikoff et al. Proc. Natl. Acad. Sci. USA, 79(6):1979-1983, 1982.*
Coleman P. M. Research in Immunology, 145:33-36, 1994.*
Foote et al. Journal of Molecular Biology, 224(2):487-499, 1992.*
Alderson, Mark R. et al., "Regulation of apoptosis and T cell activation by Fas-specific mAb," *International Immunology*, vol. 6(11):1799-1806 (1994).
Androlewicz, Matthew J. et al., "Lymphotoxin Is Expressed as a Heteromeric Complex with a Distinct 33-kDa Glycoprotein on the surface of an Activated Human T Cell Hybridoma," *The Journal of Biological Chemistry*, vol. 267(4):2542-2547 (1992).
Arulanandam, Antonio R.N. et al., "A Soluble Multimeric Recombinant CD2 Protein Identifies CD48 as a Low Affinity Ligand for Human CD2: Divergence of CD2 Ligands during the Evolution of Humans and Mice," *J. Exp. Med.*, vol. 177:1439-1450 (1993).
Bernstein, David I. et al., "Effects of therapy with an immunomodulator (imiquimod, R-837) alone and with acyclovir on genital HSV-2 infection in guinea-pigs when begun after lesion development," *Antiviral Research*, vol. 20:45-55 (1993).
Browning, Jeffrey L. et al., "Characterization of Surface Lymphotoxin Forms, Use of Specific Monoclonal Antibodies and Soluble Receptors," *The Journal of Immunology*, vol. 154:33-46 (1995).
Browning, Jeffrey L. et al., "Lymphotoxin and an Associated 33-kDa Glycoprotein are Expressed on the Surface of an Activated Human T Cell Hybridoma," *The Journal of Immunology*, vol. 147(4):1230-1237 (1991).
Browning, Jeffrey L. et al., "Lymphotoxin β, a Novel Member of the TNF Family That Forms a Heteromeric Complex with Lymphotoxin on the Cell Surface," *Cell*, vol. 72:847-856 (1993).
Browning, Jeffrey L. et al., "Signaling through the Lymphotoxin β Receptor Induces the Death of Some Adenocarcinoma Tumor Lines," *J. Exp. Med.*, vol. 183:867-878 (1996).
Browning, Jeffrey L. et al., "Signalling Through the Lymphotoxin-β Receptor in Conjunction with Interferon-γ Induces the Death of a Human Tumor Line," *The 9th International Congress of Immunology*, No. 4582 (1995).

(Continued)

*Primary Examiner*—David J. Blanchard
(74) *Attorney, Agent, or Firm*—Lahive & Cockfield, LLP; Amy E. Mandragouras, Esq.; Cristin Howley Cowles

(57) ABSTRACT

This invention concerns humanized antibodies specific for the lymphotoxin beta receptor (LT-β-R), cell lines that produce these antibodies, immunochemicals made from the antibodies, and diagnostic methods that use the antibodies. The invention also relates to the use of the antibodies alone or in combination with chemotherapeutic agent(s) in therapeutic methods.

23 Claims, 6 Drawing Sheets

OTHER PUBLICATIONS

Browning, Jeffrey L. et al., "Studies on the Differing Effects of Tumor Necrosis Factor and Lymphotoxin on the Growth of Several Human Tumor Lines," *The Journal of Immunology*, vol. 143(6):1859-1867 (1989).

Couto, Joseph R. et al., "Humanization of KC4G3, an Anti-Human Carcinoma Antibody," *Hybridoma*, vol. 13(3):215-219 (1994).

Crowe, Paul D. et al., "A Lymphotoxin-β-Specific Receptor," *Science*, vol. 264:707-710 (1994).

Crowe, Paul D. et al., "Production of lymphotoxin (LTα) and a soluble dimeric form of its receptor using the baculovirus expression system," *Journal of Immunological Methods*, vol. 168:79-89 (1994).

Dhein, Jens et al., "Induction of Apoptosis by Monoclonal Antibody Anti-Apo-1 Class Switch Variants is Dependent on Cross-Linking of APO-1 Cell Surface Antigens," *The Journal of Immunology*, vol. 149(10):3166-3173 (1992).

Dighe, Anand S. et al., "Enhanced In Vivo Growth and Resistance to Rejection of Tumor Cells Expressing Dominant Negative IFNγ Receptors," *Immunity*, vol. 1:447-456 (1994).

Düzgüneş, Nejat et al., "Liposome Targeting to HIV-Infected Cells via Recombinant Soluble CD4 and CD4-IgG (Immunoadhesin)," *Journal of Cellular Biochemistry*, p. 77, No. Q514 (1992).

Eppstein, Deborah A. et al., "Biological activity of liposome-encapsulated murine interferon γ is mediated by a cell membrane receptor," *Proc. Natl. Acad. Sci. USA*, vol. 82:3688-3692 (1985).

Fukushima, Keiko et al., "N-Linked Sugar Chain Structure of Recombinant Human Lymphotoxin Produced by CHO Cells: The Functional Role of Carbohydrate as to its Lectin-like Character and Clearance Velocity," *Archives of Biochemistry and Biophysics*, vol. 304(1):144-153 (1993).

Havell, Edward A. et al., "The Antitumor Function of Tumor Necrosis Factor (TNF), I. Therapeutic Action of TNF against as Established Murine Sarcoma Is Indirect, Immunologically Dependent, and Limited by Severe Toxicity," *J. Exp. Med.*, vol. 167:1067-1085 (1988).

He, Xiaozhong et al., "General Introduction to Modern Biological Technique," *Publishing House of Beijing Normal University*, 1st Edition, pp. 254-256 (1.8.3 &1.8.4).

Hipp, Jason D. et al., "Cancer Vaccines: An Update," *In Vivo*, vol. 14:571-585 (2000).

Hwang, Karl J. et al., "Hepatic uptake and degradation of unilamellar sphingomyelin/cholesterol liposomes: A kinetic study," *Proc. Natl. Acad. Sci. USA*, vol. 77(7):4030-4034 (1980).

Jain, Rakesh K., "Vascular and interstitial barriers to delivery of therapeutic agents in tumors," *Cancer and Metastasis Reviews*, vol. 9:253-266 (1990).

Johne, Berit et al., "Epitope mapping and binding kinetics of monoclonal antibodies studied by real time biospecific interaction analysis using surface plasmon resonance," *Journal of Immunological Methods*, vol. 160:191-198 (1993).

Juráskova, Vera et al., "Interferon inducer, polyriboguanylic—polyribocytidylic acid, inhibits experimental hepatic metastases in mice," *European Journal of Pharmacology*, vol. 221:107-111 (1992).

Kawabe, Tsutomu et al., "The Immune Responses in CD40-Deficient Mice: Impaired Immunoglobulin Class Switching and Germinal Center Formation," *Immunity*, vol. 1:167-178 (1994).

Kolanus, Waldemar et al., "T Cell Activation by Clustered Tyrosine Kinases," *Cell*, vol. 74:171-183 (1993).

Kolbinger, Frank et al., "Humanization of a mouse anti-human IgE antibody: a potential therapeutic for IgE-mediated allergies," *Protein Engineering*, vol. 6(8):971-980 (1993).

Kopp, William C. et al., "Immunomodulatory Effects of Interferon-γ in Patients with Metastatic Malignant Melanoma," *Journal of Immunotherapy*, vol. 13(3):181-190 (1993).

Lane, Peter et al., "Activated human T cells express a ligand for the human B cell-associated antigen CD40 which participates in T cell-dependent activation of B lymphocytes," *Eur. J. Immunol.*, vol. 22:2573-2578 (1992).

Langer, Robert et al., "Biocompatibility of polymeric delivery systems for macromolecules," *Journal of Biomedical Materials Research*, vol. 15:267-277 (1981).

Langer, Robert, "Controlled released of macromolecules," *Chemtech*, pp. 98-105 (1982).

Ling, Leona E. et al., "Human Type I Interferon Receptor, IFNAR, Is a Heavily Glycosylated 120-130 kD Membrane Protein," *Journal of Interferon and Cytokine Research*, vol. 15:55-61 (1995).

Loetscher, Hansruedi et al., "Recombinant 55-kDa Tumor Necrosis Factor (TNF) Receptor," *The Journal of Biological Chemistry*, vol. 266(27:18324-18329 (1991).

Morrison, Sherie L. et al., "Chimeric human antibody molecules: Mouse antigen-binding domains with human constant region domains," *Proc. Natl. Acad. Sci. USA*, vol. 81:6851-6855 (1984).

Niederle, Norbert et al., "Long-Term Treatment of Chronic Myelogenous Leukemia with Different Interferons: Results from Three Studies," *Leukemia and Lymphoma*, vol. 9:111-119 (1993).

Onishi, Tetsuro et al., "A Study on Direct Antitumor Activity of Bropirimine (Oral Interferon Inducer) for Renal Cell Carcinoma," *Acta Urol. Jpn.*, vol. 40:195-200 (1994).

Pleskov, V.M. et al., "The receptor-mediated endocytosis of influenza viruses and low-density lipoproteins by tissue cells," *Vopr. Virusol.*, vol. 39(3):121-125 (1994).

Queen, Cary et al., "A humanized antibody that binds to the interleukin 2 receptor," *Proc. Natl. Acad. Sci. USA*, vol. 86:10029-10033 (1989).

Raitano, Arthur B. et al., "Tumor Necrosis Factor Up-regulates γ-Interferon Binding in a Human Carcinoma Cell Line," *The Journal of Biological Chemistry*, vol. 265(18):10466-10472 (1990).

Riechmann, Lutz et al., "Reshaping human antibodies for therapy," *Nature*, vol. 332:323-327 (1988).

Schiller, Joan H. et al., "Biological and Clinical Effects of Intravenous Tumor Necrosis Factor-α Administered Three Times Weekly," *Cancer Research*, vol. 51:1651-1658 (1991).

Schoenfeld, Hans-Joachim et al., "Efficient Purification of Recombinant Human Tumor Necrosis Factor β from *Escherichia coli* Yields Biologically Active Protein with a Trimeric Structure That Binds to Both Tumor Necrosis Factor Receptors," *The Journal of Biological Chemistry*, vol. 266(6):3863-3869 (1991).

Sidman, Kenneth R. et al., "Controlled Release of Macromolecules and Pharmaceuticals from Synthetic Polypeptides Based on Glutamic Acid," *Biopolymers*, vol. 22:547-556 (1983).

Slepushkin, A.N. et al., "A comparative study of live and inactivated influenza vaccines: the organization of the observation and the results of a study of their reactogenicity and immunogenicity," *Vopr. Virusol.*, vol. 39(3):129-131 (1994).

Tempest, Philip R. et al., "Reshaping a Human Monoclonal Antibody to Inhibit Human Respiratory Syncytial Virus Infection In Vivo," *Bio/Technology*, vol. 9:266-271 (1991).

Traunecker, André et al., "Highly efficient neutralization of HIV with recombinant CD4-immunoglobulin molecules," *Nature*, vol. 339:68-70 (1989).

Ullrich, Axel et al., "Signal Transduction by Receptors with Tyrosine Kinase Activity," *Cell*, vol. 61:203-212 (1990).

Winter, Greg et al., "Man-made antibodies," *Nature*, vol. 349:293-299 (1991).

Xu, Jianchao et al., "Mice Deficient for the CD40 Ligand," *Immunity*, vol. 1:423-431 (1994).

Yonehara, Shin et al., "A Cell-killing Monoclonal Antibody (Anti-Fas) to a Cell Surface Antigen Co-downregulated with the Receptor of Tumor Necrosis Factor," *J. Exp. Med.*, vol. 169:1747-1756 (1989).

Kreitman, Robert J. et al., "Immunotoxins for targeted cancer therapy," *Advanced Drug Delivery Reviews*, vol. 31:53-88 (1998).

* cited by examiner

| | |
|---|---|
| 1 | ATGGGCTTCAAGATGGAGTCACAGTCTCTGGTCTTTGTATACATGTTGCTGTGGTTGTCTGGTGTTGATG |
| 71 | GAGACATTCAGATGACCCAGTCTCCTAGCTCCCTGTCCGCCTCAGTAGGAGACAGGGTCACCATCACCTG |
| 141 | CAAGGCCAGTCAGAATGTGGGTATTAATGTAGCCTGGTATCAACAGAAACCAGGGAAGGCTCCTAAATCA |
| 211 | CTGATTTCCTCGGCCTCCTACCGGTACAGTGGAGTCCCTTCCAGATTCAGCGGCAGTGGATCTGGGACAG |
| 281 | ATTTCACTCTCACCATCAGCAGCCTCCAGCCTGAAGACTTCGCAACCTATTTCTGTCAGCAATATGACAC |
| 351 | CTATCCATTCACGTTCGGCCAGGGTACCAAGGTGGAGATCAAACGAACTGTGGCTGCACCATCTGTCTTC |
| 421 | ATCTTCCCGCCATCTGATGAGCAGTTGAAATCTGGAACTGCCTCTGTTGTGTGCCTGCTGAATAACTTCT |
| 491 | ATCCCAGAGAGGCCAAAGTACAGTGGAAGGTGGATAACGCCCTCCAATCGGGTAACTCCCAGGAGAGTGT |
| 561 | CACAGAGCAGGACAGCAAGGACAGCACCTACAGCCTCAGCAGCACCCTGACGCTGAGCAAAGCAGACTAC |
| 631 | GAGAAACACAAAGTCTACGCCTGCGAAGTCACCCATCAGGGCCTGAGCTCGCCCGTCACAAAGAGCTTCA |
| 701 | ACAGGGGAGAGTGTTAG |

*Fig. 4A*

| | |
|---|---|
| 1 | MGFKMESQSL VFVYMLLWLS GVDGDIQMTQ SPSSLSASVG DRVTITCKAS QNVGINVAWY QQKPGKAPKS |
| 71 | LISSASYRYS GVPSRFSGSG SGTDFTLTIS SLQPEDFATY FCQQYDTYPF TFGQGTKVEI KRTVAAPSVF |
| 141 | IFPPSDEQLK SGTASVVCLL NNFYPREAKV QWKVDNALQS GNSQESVTEQ DSKDSTYSLS STLTLSKADY |
| 211 | EKHKVYACEV THQGLSSPVT KSFNRGEC |

*Fig. 4B*

| 1 | ATGGACTGGACCTGGAGGGTCTTCTGCTTGCTGGCTGTAGCACCAGGTGCCCACTCCCAGGTCCAACTGG |
|---|---|
| 71 | TGCAGTCTGGAGCTGAGGTGAAGAAGCCTGGGTCCTCAGTGAAGGTGTCCTGCAAGGCTTCTGGCTACAC |
| 141 | TTTCACAACCTACTATTTGCACTGGGTGAGGCAGGCCCCTGGACAGGGACTTGAGTGGATGGGATGGATT |
| 211 | TATCCTGGAAATGTTCATGCTCAGTACAATGAGAAGTTCAAGGGCAGGGTCACAATCACTGCAGACAAAT |
| 281 | CCACCAGCACAGCCTACATGGAGCTCAGCAGCCTGAGGTCTGAAGATACTGCGGTCTATTACTGTGCAAG |
| 351 | ATCCTGGGAAGGTTTTCCTTACTGGGGCCAAGGGACCACGGTCACCGTCTCCTCAGCCTCCACCAAGGGC |
| 421 | CCATCGGTCTTCCCCCTGGCACCCTCCTCCAAGAGCACCTCTGGGGGCACAGCGGCCCTGGGCTGCCTGG |
| 491 | TCAAGGACTACTTCCCCGAACCGGTGACGGTGTCGTGGAACTCAGGCGCCCTGACCAGCGGCGTGCACAC |
| 561 | CTTCCCGGCTGTCCTACAGTCCTCAGGACTCTACTCCCTCAGCAGCGTGGTGACCGTGCCCTCCAGCAGC |
| 631 | TTGGGCACCCAGACCTACATCTGCAACGTGAATCACAAGCCCAGCAACACCAAGGTGGACAAGAAAGTTG |
| 701 | AGCCCAAATCTTGTGACAAGACTCACACATGCCCACCGTGCCCAGCACCTGAACTCCTGGGGGGACCGTC |
| 771 | AGTCTTCCTCTTCCCCCCAAAACCCAAGGACACCCTCATGATCTCCCGGACCCCTGAGGTCACATGCGTG |
| 841 | GTGGTGGACGTGAGCCACGAAGACCCTGAGGTCAAGTTCAACTGGTACGTGGACGGCGTGGAGGTGCATA |
| 911 | ATGCCAAGACAAAGCCGCGGGAGGAGCAGTACAACAGCACGTACCGTGTGGTCAGCGTCCTCACCGTCCT |
| 981 | GCACCAGGACTGGCTGAATGGCAAGGAGTACAAGTGCAAGGTCTCCAACAAAGCCCTCCCAGCCCCCATC |
| 1051 | GAGAAAACCATCTCCAAAGCCAAAGGGCAGCCCCGAGAACCACAGGTGTACACCCTGCCCCCATCCCGGG |
| 1121 | ATGAGCTGACCAAGAACCAGGTCAGCCTGACCTGCCTGGTCAAAGGCTTCTATCCCAGCGACATCGCCGT |
| 1191 | GGAGTGGGAGAGCAATGGGCAGCCGGAGAACAACTACAAGACCACGCCTCCCGTGTTGGACTCCGACGGC |
| 1261 | TCCTTCTTCCTCTACAGCAAGCTCACCGTGGACAAGAGCAGGTGGCAGCAGGGGAACGTCTTCTCATGCT |
| 1331 | CCGTGATGCATGAGGCTCTGCACAACCACTACACGCAGAAGAGCCTCTCCCTGTCTCCCGGT |

*Fig. 6A*

| 1 | MDWTWRVFCL LAVAPGAHSQ VQLVQSGAEV KKPGS SVKVS CKASGYTFTT YYLHWV RQAP GQGLEWMGWI |
|---|---|
| 71 | YPGNVHAQYN EKFK GRVTIT ADKSTSTSYM ELSSL RSEDT AVYYCARSWE GFPYWG QGTT VTVSSASTKG |
| 141 | PSVFPLAPSS KSTS GGTAAL GCLVKDYFPE PVTVS WNSGA LTSGVHTFPA VLQSSG LYSL SSVVTVPSSS |
| 211 | LGTQTYI CNV NHKPSNTKVD KKVEPKSCDK THTCP PCPAP ELLGGPSVFL FPPKPK DTLM ISRTPEVTCV |
| 281 | VVDVSHEDPE VKFN WYVDGV EVHNAKTKPR EEQYN STYRV VSVLTVLHQD WLNGKE YKCK VSNKALPAPI |
| 351 | EKTISKAKGQ PREP QVYTLP PSRDELTKNQ VSLTC LVKGF YPSDIAVEWE SNGQPE NNYK TTPPVLDSDG |
| 421 | SFFLYSKLTV DKSR WQQGNV FSCSVMHEAL HNHYT QKSLS LSPG |

*Fig. 6B*

SEQUENCE LISTING

```
<160> NUMBER OF SEQ ID NOS: 62

<210> SEQ ID NO 1
<211> LENGTH: 107
<212> TYPE: PRT
<213> ORGANISM: Mus musculus

<400> SEQUENCE: 1

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Ile Asn
            20                  25                  30

Val Ala Trp Tyr Gln Gln Lys Pro Gly Gln Ser Pro Lys Ser Leu Ile
        35                  40                  45

Ser Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Glu Tyr Phe Cys Gln Gln Tyr Asp Thr Tyr Pro Phe
                85                  90                  95

Thr Phe Gly Ser Gly Thr Lys Leu Glu Ile Lys
            100                 105

<210> SEQ ID NO 2
<211> LENGTH: 116
<212> TYPE: PRT
<213> ORGANISM: Mus musculus
```

<400> SEQUENCE: 2

```
Gln Val Gln Leu Gln Gln Ser Gly Pro Glu Leu Val Lys Pro Gly Ala
 1               5                  10                  15

Ser Val Arg Ile Ser Cys Lys Ala Ser Gly Tyr Thr Phe Thr Thr Tyr
             20                  25                  30

Tyr Leu His Trp Val Lys Gln Arg Pro Gly Gln Gly Leu Glu Trp Ile
         35                  40                  45

Gly Trp Ile Tyr Pro Gly Asn Val His Ala Gln Tyr Asn Glu Lys Phe
     50                  55                  60

Lys Gly Lys Ala Thr Leu Thr Ala Asp Lys Ser Ser Thr Ala Tyr
 65                  70                  75                  80

Met Gln Leu Ser Ser Leu Thr Ser Glu Asp Ser Ala Ile Tyr Phe Cys
                 85                  90                  95

Ala Arg Ser Trp Glu Gly Phe Pro Tyr Trp Gly Gln Gly Thr Thr Val
            100                 105                 110

Thr Val Ser Ser
        115
```

<210> SEQ ID NO 3
<211> LENGTH: 321
<212> TYPE: DNA
<213> ORGANISM: Artificial Sequence
<220> FEATURE:
<221> NAME/KEY: CDS
<222> LOCATION: (1)...(321)
<223> OTHER INFORMATION: artificial humanized BHA10 variable light chain, version 1

<400> SEQUENCE: 3

```
gac att cag atg acc cag tct cct agc tcc ctg tcc gcc tca gta gga      48
Asp Ile Gln Met Thr Gln Ser Pro Ser Ser Leu Ser Ala Ser Val Gly
 1               5                  10                  15 gac agg gtc acc atc acc tgc aag gcc agt cag aat gtg ggt att aac      96
Asp Arg Val Thr Ile Thr Cys Lys Ala Ser Gln Asn Val Gly Ile Asn
             20                  25                  30 gtt gcc tgg tat caa cag aaa cca ggg aag gct cct aaa tca ctg att     144
Val Ala Trp Tyr Gln Gln Lys Pro Gly Lys Ala Pro Lys Ser Leu Ile
         35                  40                  45 tcc tcg gcc tcc tac cgg tac agt gga gtc cct tct aga ttc aca ggc     192
Ser Ser Ala Ser Tyr Arg Tyr Ser Gly Val Pro Ser Arg Phe Thr Gly
     50                  55                  60 agt gga tct ggg aca gat ttc act ctc acc atc agc agc ctg cag cct     240
Ser Gly Ser Gly Thr Asp Phe Thr Leu Thr Ile Ser Ser Leu Gln Pro
 65                  70                  75                  80 gaa gac ttc gca acc tat ttc tgt cag caa tat gac acc tat cca ttc     288
Glu Asp Phe Ala Thr Tyr Phe Cys Gln Gln Tyr Asp Thr Tyr Pro Phe
                 85                  90                  95 acg ttc ggc cag ggt acc aag gtg gag atc aaa                         321
Thr Phe Gly Gln Gly Thr Lys Val Glu Ile Lys
            100                 105
```

<210> SEQ ID NO 4
<211> LENGTH: 107
<212> TYPE: PRT
<213> ORGANISM: Artificial Sequence
<220> FEATURE:
<223> OTHER INFORMATION: artificial humanized BHA10 variable light chain, version 1

<400> SEQUENCE: 4

Asp Ile Gln Met Thr Gln Ser Pro Ser Ser Leu Ser Ala Ser Val Gly

```
                1               5                   10                  15
            Asp Arg Val Thr Ile Thr Cys Lys Ala Ser Gln Asn Val Gly Ile Asn
                        20                  25                  30

Val Ala Trp Tyr Gln Gln Lys Pro Gly Lys Ala Pro Lys Ser Leu Ile
                        35                  40                  45

Ser Ser Ala Ser Tyr Arg Tyr Ser Gly Val Pro Ser Arg Phe Thr Gly
                        50                  55                  60

Ser Gly Ser Gly Thr Asp Phe Thr Leu Thr Ile Ser Ser Leu Gln Pro
            65                      70                  75                  80

Glu Asp Phe Ala Thr Tyr Phe Cys Gln Gln Tyr Asp Thr Tyr Pro Phe
                            85                  90                  95

Thr Phe Gly Gln Gly Thr Lys Val Glu Ile Lys
                        100                 105

<210> SEQ ID NO 5
<211> LENGTH: 321
<212> TYPE: DNA
<213> ORGANISM: Artificial Sequence
<220> FEATURE:
<221> NAME/KEY: CDS
<222> LOCATION: (1)...(321)
<223> OTHER INFORMATION: artificial humanized BHA10 variable light
      chain, version 2

<400> SEQUENCE: 5 gac att cag atg acc cag tct cct agc tcc ctg tcc gcc tca gta gga         48
Asp Ile Gln Met Thr Gln Ser Pro Ser Ser Leu Ser Ala Ser Val Gly
1               5                   10                  15 gac agg gtc acc atc acc tgc aag gcc agt cag aat gtg ggt att aat         96
Asp Arg Val Thr Ile Thr Cys Lys Ala Ser Gln Asn Val Gly Ile Asn
            20                  25                  30 gta gcc tgg tat caa cag aaa cca ggg aag gct cct aaa tca ctg att        144
Val Ala Trp Tyr Gln Gln Lys Pro Gly Lys Ala Pro Lys Ser Leu Ile
        35                  40                  45 tcc tcg gcc tcc tac cgg tac agt gga gtc cct tcc aga ttc agc ggc        192
Ser Ser Ala Ser Tyr Arg Tyr Ser Gly Val Pro Ser Arg Phe Ser Gly
    50                  55                  60 agt gga tct ggg aca gat ttc act ctc acc atc agc agc ctc cag cct        240
Ser Gly Ser Gly Thr Asp Phe Thr Leu Thr Ile Ser Ser Leu Gln Pro
65                  70                  75                  80 gaa gac ttc gca acc tat ttc tgt cag caa tat gac acc tat cca ttc        288
Glu Asp Phe Ala Thr Tyr Phe Cys Gln Gln Tyr Asp Thr Tyr Pro Phe
                85                  90                  95 acg ttc ggc cag ggt acc aag gtg gag atc aaa                            321
Thr Phe Gly Gln Gly Thr Lys Val Glu Ile Lys
            100                 105

<210> SEQ ID NO 6
<211> LENGTH: 107
<212> TYPE: PRT
<213> ORGANISM: Artificial Sequence
<220> FEATURE:
<223> OTHER INFORMATION: artificial humanized BHA10 variable light
      chain, version 2

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Ile Asn
            20                  25                  30

Val Ala Trp Tyr Gln Gln Lys Pro Gly Lys Ala Pro Lys Ser Leu Ile
```

```
                    35                  40                  45
Ser Ser Ala Ser Tyr Arg Tyr Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Tyr Asp Thr Tyr Pro Phe
                 85                  90                  95

Thr Phe Gly Gln Gly Thr Lys Val Glu Ile Lys
                100                 105

<210> SEQ ID NO 7
<211> LENGTH: 321
<212> TYPE: DNA
<213> ORGANISM: Artificial Sequence
<220> FEATURE:
<221> NAME/KEY: CDS
<222> LOCATION: (1)...(321)
<223> OTHER INFORMATION: artificial humanized BHA10 variable light
      chain, version 3

<400> SEQUENCE: 7 gac att cag atg acc cag tct cct agc tcc ctg tcc gcc tca gta gga      48
Asp Ile Gln Met Thr Gln Ser Pro Ser Ser Leu Ser Ala Ser Val Gly
 1               5                  10                  15 gac agg gtc acc atc acc tgc aag gcc agt cag aat gtg ggt att aat      96
Asp Arg Val Thr Ile Thr Cys Lys Ala Ser Gln Asn Val Gly Ile Asn
                20                  25                  30 gta gcc tgg ttc caa cag aaa ccc ggg aag gct cct aaa tca ctg att     144
Val Ala Trp Phe Gln Gln Lys Pro Gly Lys Ala Pro Lys Ser Leu Ile
         35                  40                  45 tcc tcg gcc tcc tac cgg tac agt gga gtc cct tct aga ttc agc ggc     192
Ser Ser Ala Ser Tyr Arg Tyr Ser Gly Val Pro Ser Arg Phe Ser Gly
         50                  55                  60 agt gga tct ggg aca gat ttc act ctc acc atc agc agc ctg cag cct     240
Ser Gly Ser Gly Thr Asp Phe Thr Leu Thr Ile Ser Ser Leu Gln Pro
 65                  70                  75                  80 gaa gac ttc gca acc tat tac tgt cag caa tat gac acc tat cca ttc     288
Glu Asp Phe Ala Thr Tyr Tyr Cys Gln Gln Tyr Asp Thr Tyr Pro Phe
                 85                  90                  95 acg ttc ggc cag ggt acc aag gtg gag atc aaa                         321
Thr Phe Gly Gln Gly Thr Lys Val Glu Ile Lys
                100                 105

<210> SEQ ID NO 8
<211> LENGTH: 107
<212> TYPE: PRT
<213> ORGANISM: Artificial Sequence
<220> FEATURE:
<223> OTHER INFORMATION: artificial humanized BHA10 variable light
      chain, version 3

<400> SEQUENCE: 8

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asn Val Gly Ile Asn
                20                  25                  30

Val Ala Trp Phe Gln Gln Lys Pro Gly Lys Ala Pro Lys Ser Leu Ile
         35                  40                  45

Ser Ser Ala Ser Tyr Arg Tyr Ser Gly Val Pro Ser Arg Phe Ser Gly
         50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Tyr Asp Thr Tyr Pro Phe
                    85                  90                  95

Thr Phe Gly Gln Gly Thr Lys Val Glu Ile Lys
            100                 105

<210> SEQ ID NO 9
<211> LENGTH: 348
<212> TYPE: DNA
<213> ORGANISM: Artificial Sequence
<220> FEATURE:
<221> NAME/KEY: CDS
<222> LOCATION: (1)...(348)
<223> OTHER INFORMATION: artificial humanized BHA10 variable heavy
      chain, version 1

<400> SEQUENCE: 9 cag gtc caa ctg gtg cag tct gga gct gag gtg aag aag cct ggg tcc        48
Gln Val Gln Leu Val Gln Ser Gly Ala Glu Val Lys Lys Pro Gly Ser
  1               5                  10                  15 tca gtg aag gtg tcc tgc aag gct tct ggc tac act ttc aca acc tac        96
Ser Val Lys Val Ser Cys Lys Ala Ser Gly Tyr Thr Phe Thr Thr Tyr
                 20                  25                  30 tat ttg cac tgg gtg agg cag gcc cct gga cag gga ctt gag tgg att       144
Tyr Leu His Trp Val Arg Gln Ala Pro Gly Gln Gly Leu Glu Trp Ile
             35                  40                  45 gga tgg att tat cct gga aat gtt cat gct cag tac aat gag aag ttc       192
Gly Trp Ile Tyr Pro Gly Asn Val His Ala Gln Tyr Asn Glu Lys Phe
         50                  55                  60 aag ggc agg gcc aca ctg aca gca gac aaa tcc acc agc aca gcc tac       240
Lys Gly Arg Ala Thr Leu Thr Ala Asp Lys Ser Thr Ser Thr Ala Tyr
 65                  70                  75                  80 atg gag ctc agc agc ctg agg tct gaa gat act gcg gtc tat ttc tgt       288
Met Glu Leu Ser Ser Leu Arg Ser Glu Asp Thr Ala Val Tyr Phe Cys
                 85                  90                  95 gca aga tcc tgg gaa ggt ttt cct tac tgg ggc caa ggg acc acg gtc       336
Ala Arg Ser Trp Glu Gly Phe Pro Tyr Trp Gly Gln Gly Thr Thr Val
            100                 105                 110 acc gtc tcc tca                                                       348
Thr Val Ser Ser
        115

<210> SEQ ID NO 10
<211> LENGTH: 116
<212> TYPE: PRT
<213> ORGANISM: Artificial Sequence
<220> FEATURE:
<223> OTHER INFORMATION: artificial humanized BHA10 variable heavy chain
      version 1

<400> SEQUENCE: 10

Gln Val Gln Leu Val Gln Ser Gly Ala Glu Val Lys Lys Pro Gly Ser
  1               5                  10                  15

Ser Val Lys Val Ser Cys Lys Ala Ser Gly Tyr Thr Phe Thr Thr Tyr
                 20                  25                  30

Tyr Leu His Trp Val Arg Gln Ala Pro Gly Gln Gly Leu Glu Trp Ile
             35                  40                  45

Gly Trp Ile Tyr Pro Gly Asn Val His Ala Gln Tyr Asn Glu Lys Phe
         50                  55                  60

Lys Gly Arg Ala Thr Leu Thr Ala Asp Lys Ser Thr Ser Thr Ala Tyr
 65                  70                  75                  80
```

```
Met Glu Leu Ser Ser Leu Arg Ser Glu Asp Thr Ala Val Tyr Phe Cys
             85                  90                  95

Ala Arg Ser Trp Glu Gly Phe Pro Tyr Trp Gly Gln Gly Thr Thr Val
            100                 105                 110

Thr Val Ser Ser
        115

<210> SEQ ID NO 11
<211> LENGTH: 348
<212> TYPE: DNA
<213> ORGANISM: Artificial Sequence
<220> FEATURE:
<221> NAME/KEY: CDS
<222> LOCATION: (1)...(348)
<223> OTHER INFORMATION: artificial humanized BHA10 variable heavy chain
      version 2

<400> SEQUENCE: 11 cag gtc caa ctg gtg cag tct gga gct gag gtg aag aag cct ggg tcc        48
Gln Val Gln Leu Val Gln Ser Gly Ala Glu Val Lys Lys Pro Gly Ser
 1               5                  10                  15 tca gtg aag gtg tcc tgc aag gct tct ggc tac act ttc aca acc tac        96
Ser Val Lys Val Ser Cys Lys Ala Ser Gly Tyr Thr Phe Thr Thr Tyr
             20                  25                  30 tat ttg cac tgg gtg agg cag gcc cct gga cag gga ctt gag tgg att       144
Tyr Leu His Trp Val Arg Gln Ala Pro Gly Gln Gly Leu Glu Trp Ile
         35                  40                  45 gga tgg att tat cct gga aat gtt cat gct cag tac aat gag aag ttc       192
Gly Trp Ile Tyr Pro Gly Asn Val His Ala Gln Tyr Asn Glu Lys Phe
     50                  55                  60 aag ggc agg gcc aca atc act gca gac aaa tcc acc agc aca gcc tac       240
Lys Gly Arg Ala Thr Ile Thr Ala Asp Lys Ser Thr Ser Thr Ala Tyr
 65                  70                  75                  80 atg gag ctc agc agc ctg agg tct gaa gat act gcg gtc tat tac tgt       288
Met Glu Leu Ser Ser Leu Arg Ser Glu Asp Thr Ala Val Tyr Tyr Cys
                 85                  90                  95 gca aga tcc tgg gaa ggt ttt cct tac tgg ggc caa ggg acc acg gtc       336
Ala Arg Ser Trp Glu Gly Phe Pro Tyr Trp Gly Gln Gly Thr Thr Val
            100                 105                 110 acc gtc tcc tca                                                        348
Thr Val Ser Ser
        115

<210> SEQ ID NO 12
<211> LENGTH: 116
<212> TYPE: PRT
<213> ORGANISM: Artificial Sequence
<220> FEATURE:
<223> OTHER INFORMATION: Amino acid sequence of humanized BHA10 heavy
      chain variable domain (version 2-VH#2)

<400> SEQUENCE: 12

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Thr Tyr
             20                  25                  30

Tyr Leu His Trp Val Arg Gln Ala Pro Gly Gln Gly Leu Glu Trp Ile
         35                  40                  45

Gly Trp Ile Tyr Pro Gly Asn Val His Ala Gln Tyr Asn Glu Lys Phe
     50                  55                  60

Lys Gly Arg Ala Thr Ile Thr Ala Asp Lys Ser Thr Ser Thr Ala Tyr
 65                  70                  75                  80
```

```
Met Glu Leu Ser Ser Leu Arg Ser Glu Asp Thr Ala Val Tyr Tyr Cys
            85                  90                  95

Ala Arg Ser Trp Glu Gly Phe Pro Tyr Trp Gly Gln Gly Thr Thr Val
           100                 105                 110

Thr Val Ser Ser
        115

<210> SEQ ID NO 13
<211> LENGTH: 348
<212> TYPE: DNA
<213> ORGANISM: Artificial Sequence
<220> FEATURE:
<223> OTHER INFORMATION: artificial humanized BHA10 variable heavy
      chain, version 3
<220> FEATURE:
<221> NAME/KEY: CDS
<222> LOCATION: (1)...(348)

<400> SEQUENCE: 13 cag gtc caa ctg gtg cag tct gga gct gag gtg aag aag cct ggg tcc      48
Gln Val Gln Leu Val Gln Ser Gly Ala Glu Val Lys Lys Pro Gly Ser
 1               5                  10                  15 tca gtg aag gtg tcc tgc aag gct tct ggc tac act ttc aca acc tac      96
Ser Val Lys Val Ser Cys Lys Ala Ser Gly Tyr Thr Phe Thr Thr Tyr
            20                  25                  30 tat ttg cac tgg gtg agg cag gcc cct gga cag gga ctt gag tgg atg     144
Tyr Leu His Trp Val Arg Gln Ala Pro Gly Gln Gly Leu Glu Trp Met
        35                  40                  45 gga tgg att tat cct gga aat gtt cat gct cag tac aat gag aag ttc     192
Gly Trp Ile Tyr Pro Gly Asn Val His Ala Gln Tyr Asn Glu Lys Phe
    50                  55                  60 aag ggc agg gtc aca atc act gca gac aaa tcc acc agc aca gcc tac     240
Lys Gly Arg Val Thr Ile Thr Ala Asp Lys Ser Thr Ser Thr Ala Tyr
65                  70                  75                  80 atg gag ctc agc agc ctg agg tct gaa gat act gcg gtc tat tac tgt     288
Met Glu Leu Ser Ser Leu Arg Ser Glu Asp Thr Ala Val Tyr Tyr Cys
                85                  90                  95 gca aga tcc tgg gaa ggt ttt cct tac tgg ggc caa ggg acc acg gtc     336
Ala Arg Ser Trp Glu Gly Phe Pro Tyr Trp Gly Gln Gly Thr Thr Val
           100                 105                 110 acc gtc tcc tca                                                     348
Thr Val Ser Ser
        115

<210> SEQ ID NO 14
<211> LENGTH: 116
<212> TYPE: PRT
<213> ORGANISM: Artificial Sequence
<220> FEATURE:
<223> OTHER INFORMATION: Amino acid sequence of humanized BHA10 heavy
      chain variable domain (version 3-VH#3)

<400> SEQUENCE: 14

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Thr Tyr
            20                  25                  30

Tyr Leu His Trp Val Arg Gln Ala Pro Gly Gln Gly Leu Glu Trp Met
        35                  40                  45

Gly Trp Ile Tyr Pro Gly Asn Val His Ala Gln Tyr Asn Glu Lys Phe
    50                  55                  60
```

```
Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Trp Glu Gly Phe Pro Tyr Trp Gly Gln Gly Thr Thr Val
            100                 105                 110

Thr Val Ser Ser
        115
```

<210> SEQ ID NO 15
<211> LENGTH: 214
<212> TYPE: PRT
<213> ORGANISM: Artificial Sequence
<220> FEATURE:
<223> OTHER INFORMATION: artificial humanized BHA10 light chain,
      version 4

<400> SEQUENCE: 15

```
Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Asn Val Gly Ile Asn
             20                  25                  30

Val Ala Trp Tyr Gln Gln Lys Pro Gly Lys Ala Pro Lys Ser Leu Ile
         35                  40                  45

Ser Ser Ala Ser Tyr Arg Tyr Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Tyr Asp Thr Tyr Pro Phe
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 16
<211> LENGTH: 445
<212> TYPE: PRT
<213> ORGANISM: Artificial Sequence
<220> FEATURE:
<223> OTHER INFORMATION: artificial humanized BHA10 heavy chain,
      version 3

<400> SEQUENCE: 16

```
Gln Val Gln Leu Val Gln Ser Gly Ala Glu Val Lys Lys Pro Gly Ser
  1               5                  10                  15
```

-continued

```
Ser Val Lys Val Ser Cys Lys Ala Ser Gly Tyr Thr Phe Thr Thr Tyr
             20                  25                  30
Tyr Leu His Trp Val Arg Gln Ala Pro Gly Gln Gly Leu Glu Trp Met
             35                  40                  45
Gly Trp Ile Tyr Pro Gly Asn Val His Ala Gln Tyr Asn Glu Lys Phe
 50                  55                  60
Lys Gly Arg Val Thr Ile Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
             85                  90                  95
Ala Arg Ser Trp Glu Gly Phe Pro Tyr Trp Gly Gln Gly Thr Thr Val
            100                 105                 110
Thr Val Ser Ser Ala Ser Thr Lys Gly Pro Ser Val Phe Pro Leu Ala
            115                 120                 125
Pro Ser Ser Lys Ser Thr Ser Gly Gly Thr Ala Ala Leu Gly Cys Leu
130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
            165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
            195                 200                 205
Lys Val Asp Lys Lys Val Glu Pro Lys Ser Cys Asp Lys Thr His Thr
210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
            245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
            275                 280                 285
Lys Pro Arg Glu Glu Gln Tyr Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
            325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
            370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
            405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly
```

<210> SEQ ID NO 17
<211> LENGTH: 31
<212> TYPE: DNA
<213> ORGANISM: Artificial Sequence
<220> FEATURE:
<223> OTHER INFORMATION: primers

<400> SEQUENCE: 17
tgaggagacg gtgaccgtgg cccttggccc c                               31

<210> SEQ ID NO 18
<211> LENGTH: 22
<212> TYPE: DNA
<213> ORGANISM: Artificial Sequence
<220> FEATURE:
<223> OTHER INFORMATION: primers
<220> FEATURE:
<221> NAME/KEY: misc_feature
<222> LOCATION: 5,15
<223> OTHER INFORMATION: S = Cys or Gly
<220> FEATURE:
<221> NAME/KEY: misc_feature
<222> LOCATION: 6
<223> OTHER INFORMATION: M = Ala or Cys
<220> FEATURE:
<221> NAME/KEY: misc_feature
<222> LOCATION: 8
<223> OTHER INFORMATION: R = Ala or Gly
<220> FEATURE:
<221> NAME/KEY: misc_feature
<222> LOCATION: 20
<223> OTHER INFORMATION: W = Ala or Thr

<400> SEQUENCE: 18
aggtsmarct gcagsagtcw gg                                         22

<210> SEQ ID NO 19
<211> LENGTH: 41
<212> TYPE: DNA
<213> ORGANISM: Artificial Sequence
<220> FEATURE:
<223> OTHER INFORMATION: primers
<220> FEATURE:
<221> NAME/KEY: misc_feature
<222> LOCATION: 35
<223> OTHER INFORMATION: K = Gly or Thr
<220> FEATURE:
<221> NAME/KEY: misc_feature
<222> LOCATION: 17, 35
<223> OTHER INFORMATION: W = Ala or Thr
<220> FEATURE:
<221> NAME/KEY: misc_feature
<222> LOCATION: 36, 37
<223> OTHER INFORMATION: Y = Cys or Thr

<400> SEQUENCE: 19
actagtcgac atgggcwtca agatggagtc acakwyycwg g                    41

<210> SEQ ID NO 20
<211> LENGTH: 22
<212> TYPE: DNA
<213> ORGANISM: Artificial Sequence
<220> FEATURE:
<223> OTHER INFORMATION: primers

<400> SEQUENCE: 20
gttagatctc cagcttggtc cc                                         22

```
<210> SEQ ID NO 21
<211> LENGTH: 10
<212> TYPE: PRT
<213> ORGANISM: Mus musculus

<400> SEQUENCE: 21

Asp Ile Val Met Thr Gln Ser Gln Lys Phe
 1               5                  10

<210> SEQ ID NO 22
<211> LENGTH: 16
<212> TYPE: PRT
<213> ORGANISM: Mus musculus

<400> SEQUENCE: 22

Gln Val Gln Leu Gln Gln Ser Gly Pro Glu Leu Val Lys Pro Gly Ala
 1               5                  10                  15

<210> SEQ ID NO 23
<211> LENGTH: 9
<212> TYPE: PRT
<213> ORGANISM: Mus musculus

<400> SEQUENCE: 23

Gln Val Gln Leu Gln Gln Ser Gly Pro
 1               5

<210> SEQ ID NO 24
<211> LENGTH: 35
<212> TYPE: DNA
<213> ORGANISM: Artificial Sequence
<220> FEATURE:
<223> OTHER INFORMATION: primers

<400> SEQUENCE: 24
gcactgggtg aggcaggccc ctggacaggg acttg                        35

<210> SEQ ID NO 25
<211> LENGTH: 33
<212> TYPE: DNA
<213> ORGANISM: Artificial Sequence
<220> FEATURE:
<223> OTHER INFORMATION: primers

<400> SEQUENCE: 25
cccaggtcca actggtgcag tctggagctg agg                          33

<210> SEQ ID NO 26
<211> LENGTH: 112
<212> TYPE: DNA
<213> ORGANISM: Artificial Sequence
<220> FEATURE:
<223> OTHER INFORMATION: primers

<400> SEQUENCE: 26
gaagttcaag ggcagggcca cactgacagc agacaaatcc accagcacag cctacatgga    60
gctcagcagc ctgaggtctg aagatactgc ggtctatttc tgtgcaagat cc           112

<210> SEQ ID NO 27
<211> LENGTH: 71
<212> TYPE: DNA
<213> ORGANISM: Artificial Sequence
<220> FEATURE:
<223> OTHER INFORMATION: primers

<400> SEQUENCE: 27
```
caggtccaac tggtgcagtc tggagctgag gtgaagaagc ctgggtcctc agtgaaggtg    60
tcctgcaagg c    71

<210> SEQ ID NO 28
<211> LENGTH: 35
<212> TYPE: DNA
<213> ORGANISM: Artificial Sequence
<220> FEATURE:
<223> OTHER INFORMATION: primers

<400> SEQUENCE: 28
gcactgggtg aggcaggccc ctggacaggg acttg    35

<210> SEQ ID NO 29
<211> LENGTH: 112
<212> TYPE: DNA
<213> ORGANISM: Artificial Sequence
<220> FEATURE:
<223> OTHER INFORMATION: primers

<400> SEQUENCE: 29
gaagttcaag ggcagggcca caatcactgc agacaaatcc accagcacag cctacatgga    60
gctcagcagc ctgaggtctg aagatactgc ggtctattac tgtgcaagat cc    112

<210> SEQ ID NO 30
<211> LENGTH: 71
<212> TYPE: DNA
<213> ORGANISM: Artificial Sequence
<220> FEATURE:
<223> OTHER INFORMATION: primers

<400> SEQUENCE: 30
caggtccaac tggtgcagtc tggagctgag gtgaagaagc ctgggtcctc agtgaaggtg    60
tcctgcaagg c    71

<210> SEQ ID NO 31
<211> LENGTH: 112
<212> TYPE: DNA
<213> ORGANISM: Artificial Sequence
<220> FEATURE:
<223> OTHER INFORMATION: primers

<400> SEQUENCE: 31
gaagttcaag ggcagggtca caatcactgc agacaaatcc accagcacag cctacatgga    60
gctcagcagc ctgaggtctg aagatactgc ggtctattac tgtgcaagat cc    112

<210> SEQ ID NO 32
<211> LENGTH: 45
<212> TYPE: DNA
<213> ORGANISM: Artificial Sequence
<220> FEATURE:
<223> OTHER INFORMATION: primers

<400> SEQUENCE: 32
ggcccctgga cagggacttg agtggatggg atggatttat cctgg    45

<210> SEQ ID NO 33
<211> LENGTH: 80
<212> TYPE: DNA
<213> ORGANISM: Artificial Sequence
<220> FEATURE:
<223> OTHER INFORMATION: primers -continued

```
<400> SEQUENCE: 33
gatggagaca ttcagatgac ccagtctcct agctccctgt ccgcctcagt aggagacagg    60
gtcaccatca cctgcaaggc                                                80

<210> SEQ ID NO 34
<211> LENGTH: 43
<212> TYPE: DNA
<213> ORGANISM: Artificial Sequence
<220> FEATURE:
<223> OTHER INFORMATION: primers

<400> SEQUENCE: 34
gtagcctggt tccaacagaa acccgggaag gctcctaaat cac                      43

<210> SEQ ID NO 35
<211> LENGTH: 30
<212> TYPE: DNA
<213> ORGANISM: Artificial Sequence
<220> FEATURE:
<223> OTHER INFORMATION: primers

<400> SEQUENCE: 35
cagtggagtc ccttctagat tcacaggcag                                     30

<210> SEQ ID NO 36
<211> LENGTH: 52
<212> TYPE: DNA
<213> ORGANISM: Artificial Sequence
<220> FEATURE:
<223> OTHER INFORMATION: primers

<400> SEQUENCE: 36
ctcaccatca gcagcctgca gcctgaagac ttcgcaacct atttctgtca gc             52

<210> SEQ ID NO 37
<211> LENGTH: 45
<212> TYPE: DNA
<213> ORGANISM: Artificial Sequence
<220> FEATURE:
<223> OTHER INFORMATION: primers

<400> SEQUENCE: 37
gggtattaat gtagcctggt atcaacagaa accagggaag gctcc                    45

<210> SEQ ID NO 38
<211> LENGTH: 52
<212> TYPE: DNA
<213> ORGANISM: Artificial Sequence
<220> FEATURE:
<223> OTHER INFORMATION: primers

<400> SEQUENCE: 38
cctatccatt cacgttcggc cagggtacca aggtggagat ctaacaaggg cg             52

<210> SEQ ID NO 39
<211> LENGTH: 39
<212> TYPE: DNA
<213> ORGANISM: Artificial Sequence
<220> FEATURE:
<223> OTHER INFORMATION: primers

<400> SEQUENCE: 39
ccctggtttc tgttgatacc aggcaacgtt aatacccac                           39
```

<210> SEQ ID NO 40
<211> LENGTH: 80
<212> TYPE: DNA
<213> ORGANISM: Artificial Sequence
<220> FEATURE:
<223> OTHER INFORMATION: primers

<400> SEQUENCE: 40
gatggagaca ttcagatgac ccagtctcct agctccctgt ccgcctcagt aggagacagg    60
gtcaccatca cctgcaaggc                                                80

<210> SEQ ID NO 41
<211> LENGTH: 43
<212> TYPE: DNA
<213> ORGANISM: Artificial Sequence
<220> FEATURE:
<223> OTHER INFORMATION: primers

<400> SEQUENCE: 41
gtagcctggt tccaacagaa acccgggaag gctcctaaat cac                       43

<210> SEQ ID NO 42
<211> LENGTH: 36
<212> TYPE: DNA
<213> ORGANISM: Artificial Sequence
<220> FEATURE:
<223> OTHER INFORMATION: primers

<400> SEQUENCE: 42
cagtggagtc ccttctagat tcagcggcag tggatc                               36

<210> SEQ ID NO 43
<211> LENGTH: 52
<212> TYPE: DNA
<213> ORGANISM: Artificial Sequence
<220> FEATURE:
<223> OTHER INFORMATION: primers

<400> SEQUENCE: 43
ctcaccatca gcagcctgca gcctgaagac ttcgcaacct atttctgtca gc              52

<210> SEQ ID NO 44
<211> LENGTH: 48
<212> TYPE: DNA
<213> ORGANISM: Artificial Sequence
<220> FEATURE:
<223> OTHER INFORMATION: primers

<400> SEQUENCE: 44
gctgacagaa ataggttgcg aagtcttcag gctggaggct gctgatgg                  48

<210> SEQ ID NO 45
<211> LENGTH: 44
<212> TYPE: DNA
<213> ORGANISM: Artificial Sequence
<220> FEATURE:
<223> OTHER INFORMATION: primers

<400> SEQUENCE: 45
ggtacagtgg agtcccttcc agattcagcg gcagtggatc tggg                      44

<210> SEQ ID NO 46
<211> LENGTH: 45
<212> TYPE: DNA
<213> ORGANISM: Artificial Sequence
<220> FEATURE:

```
<223> OTHER INFORMATION: primers

<400> SEQUENCE: 46
gggtattaat gtagcctggt atcaacagaa accagggaag gctcc                45

<210> SEQ ID NO 47
<211> LENGTH: 52
<212> TYPE: DNA
<213> ORGANISM: Artificial Sequence
<220> FEATURE:
<223> OTHER INFORMATION: primers

<400> SEQUENCE: 47
cctatccatt cacgttcggc cagggtacca aggtggagat ctaacaaggg cg         52

<210> SEQ ID NO 48
<211> LENGTH: 80
<212> TYPE: DNA
<213> ORGANISM: Artificial Sequence
<220> FEATURE:
<223> OTHER INFORMATION: primers

<400> SEQUENCE: 48
gatggagaca ttcagatgac ccagtctcct agctccctgt ccgcctcagt aggagacagg     60
gtcaccatca cctgcaaggc                                                 80

<210> SEQ ID NO 49
<211> LENGTH: 43
<212> TYPE: DNA
<213> ORGANISM: Artificial Sequence
<220> FEATURE:
<223> OTHER INFORMATION: primers

<400> SEQUENCE: 49
gtagcctggt tccaacagaa acccgggaag gctcctaaat cac                   43

<210> SEQ ID NO 50
<211> LENGTH: 36
<212> TYPE: DNA
<213> ORGANISM: Artificial Sequence
<220> FEATURE:
<223> OTHER INFORMATION: primers

<400> SEQUENCE: 50
cagtggagtc ccttctagat tcagcggcag tggatc                           36

<210> SEQ ID NO 51
<211> LENGTH: 58
<212> TYPE: DNA
<213> ORGANISM: Artificial Sequence
<220> FEATURE:
<223> OTHER INFORMATION: primers

<400> SEQUENCE: 51
ctcaccatca gcagcctgca gcctgaagac ttcgcaacct attactgtca gcaatatg   58

<210> SEQ ID NO 52
<211> LENGTH: 52
<212> TYPE: DNA
<213> ORGANISM: Artificial Sequence
<220> FEATURE:
<223> OTHER INFORMATION: primers

<400> SEQUENCE: 52
cctatccatt cacgttcggc cagggtacca aggtggagat ctaacaaggg cg         52
```

<210> SEQ ID NO 53
<211> LENGTH: 31
<212> TYPE: DNA
<213> ORGANISM: Artificial Sequence
<220> FEATURE:
<223> OTHER INFORMATION: primers

<400> SEQUENCE: 53
cggatcctca accgggagac agggagaggc t                         31

<210> SEQ ID NO 54
<211> LENGTH: 28
<212> TYPE: DNA
<213> ORGANISM: Artificial Sequence
<220> FEATURE:
<223> OTHER INFORMATION: primers

<400> SEQUENCE: 54
cggatcccta acactctccc ctgttgaa                             28

<210> SEQ ID NO 55
<211> LENGTH: 30
<212> TYPE: DNA
<213> ORGANISM: Artificial Sequence
<220> FEATURE:
<223> OTHER INFORMATION: primers

<400> SEQUENCE: 55
gctagcggat ccaccatgga ctggacctgg                           30

<210> SEQ ID NO 56
<211> LENGTH: 31
<212> TYPE: DNA
<213> ORGANISM: Artificial Sequence
<220> FEATURE:
<223> OTHER INFORMATION: primers

<400> SEQUENCE: 56
cggatcctca accgggagac agggagaggc t                         31

<210> SEQ ID NO 57
<211> LENGTH: 33
<212> TYPE: DNA
<213> ORGANISM: Artificial Sequence
<220> FEATURE:
<223> OTHER INFORMATION: primers

<400> SEQUENCE: 57
cccttaggat ccaccatggg cttcaagatg gag                       33

<210> SEQ ID NO 58
<211> LENGTH: 28
<212> TYPE: DNA
<213> ORGANISM: Mus musculus
<220> FEATURE:
<223> OTHER INFORMATION: primers

<400> SEQUENCE: 58
cggatcccta acactctccc ctgttgaa                             28

<210> SEQ ID NO 59
<211> LENGTH: 717
<212> TYPE: DNA
<213> ORGANISM: Artificial Sequence
<220> FEATURE:

<223> OTHER INFORMATION: Humanized BHA10, light chain, version # 2
<220> FEATURE:
<221> NAME/KEY: CDS
<222> LOCATION: (1)...(716)

<400> SEQUENCE: 59

```
atg ggc ttc aag atg gag tca cag tct ctg gtc ttt gta tac atg ttg        48
Met Gly Phe Lys Met Glu Ser Gln Ser Leu Val Phe Val Tyr Met Leu
1               5                   10                  15 ctg tgg ttg tct ggt gtt gat gga gac att cag atg acc cag tct cct        96
Leu Trp Leu Ser Gly Val Asp Gly Asp Ile Gln Met Thr Gln Ser Pro
                20                  25                  30 agc tcc ctg tcc gcc tca gta gga gac agg gtc acc atc acc tgc aag       144
Ser Ser Leu Ser Ala Ser Val Gly Asp Arg Val Thr Ile Thr Cys Lys
            35                  40                  45 gcc agt cag aat gtg ggt att aat gta gcc tgg tat caa cag aaa cca       192
Ala Ser Gln Asn Val Gly Ile Asn Val Ala Trp Tyr Gln Gln Lys Pro
        50                  55                  60 ggg aag gct cct aaa tca ctg att tcc tcg gcc tcc tac cgg tac agt       240
Gly Lys Ala Pro Lys Ser Leu Ile Ser Ser Ala Ser Tyr Arg Tyr Ser
65                  70                  75                  80 gga gtc cct tcc aga ttc agc ggc agt gga tct ggg aca gat ttc act       288
Gly Val Pro Ser Arg Phe Ser Gly Ser Gly Ser Gly Thr Asp Phe Thr
                85                  90                  95 ctc acc atc agc agc ctc cag cct gaa gac ttc gca acc tat ttc tgt       336
Leu Thr Ile Ser Ser Leu Gln Pro Glu Asp Phe Ala Thr Tyr Phe Cys
                100                 105                 110 cag caa tat gac acc tat cca ttc acg ttc ggc cag ggt acc aag gtg       384
Gln Gln Tyr Asp Thr Tyr Pro Phe Thr Phe Gly Gln Gly Thr Lys Val
            115                 120                 125 gag atc aaa cga act gtg gct gca cca tct gtc ttc atc ttc ccg cca       432
Glu Ile Lys Arg Thr Val Ala Ala Pro Ser Val Phe Ile Phe Pro Pro
        130                 135                 140 tct gat gag cag ttg aaa tct gga act gcc tct gtt gtg tgc ctg ctg       480
Ser Asp Glu Gln Leu Lys Ser Gly Thr Ala Ser Val Val Cys Leu Leu
145                 150                 155                 160 aat aac ttc tat ccc aga gag gcc aaa gta cag tgg aag gtg gat aac       528
Asn Asn Phe Tyr Pro Arg Glu Ala Lys Val Gln Trp Lys Val Asp Asn
                165                 170                 175 gcc ctc caa tcg ggt aac tcc cag gag agt gtc aca gag cag gac agc       576
Ala Leu Gln Ser Gly Asn Ser Gln Glu Ser Val Thr Glu Gln Asp Ser
            180                 185                 190 aag gac agc acc tac agc ctc agc agc acc ctg acg ctg agc aaa gca       624
Lys Asp Ser Thr Tyr Ser Leu Ser Ser Thr Leu Thr Leu Ser Lys Ala
        195                 200                 205 gac tac gag aaa cac aaa gtc tac gcc tgc gaa gtc acc cat cag ggc       672
Asp Tyr Glu Lys His Lys Val Tyr Ala Cys Glu Val Thr His Gln Gly
    210                 215                 220 ctg agc tcg ccc gtc aca aag agc ttc aac agg gga gag tgt tag           717
Leu Ser Ser Pro Val Thr Lys Ser Phe Asn Arg Gly Glu Cys
225                 230                 235
```

<210> SEQ ID NO 60
<211> LENGTH: 238
<212> TYPE: PRT
<213> ORGANISM: Artificial Sequence
<220> FEATURE:
<223> OTHER INFORMATION: Humanized BHA10, light chain, version # 2

<400> SEQUENCE: 60

```
Met Gly Phe Lys Met Glu Ser Gln Ser Leu Val Phe Val Tyr Met Leu
1               5                   10                  15
```

```
Leu Trp Leu Ser Gly Val Asp Gly Asp Ile Gln Met Thr Gln Ser Pro
        20                  25                  30

Ser Ser Leu Ser Ala Ser Val Gly Asp Arg Val Thr Ile Thr Cys Lys
        35                  40                  45

Ala Ser Gln Asn Val Gly Ile Asn Val Ala Trp Tyr Gln Gln Lys Pro
        50                  55                  60

Gly Lys Ala Pro Lys Ser Leu Ile Ser Ser Ala Ser Tyr Arg Tyr Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Phe Cys
            100                 105                 110

Gln Gln Tyr Asp Thr Tyr Pro Phe Thr Phe Gly Gln Gly Thr Lys Val
            115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys
225                 230                 235

<210> SEQ ID NO 61
<211> LENGTH: 1392
<212> TYPE: DNA
<213> ORGANISM: Artificial Sequence
<220> FEATURE:
<223> OTHER INFORMATION: Humanized BHA10, heavy chain, version # 3
<220> FEATURE:
<221> NAME/KEY: CDS
<222> LOCATION: (1)...(1392)

<400> SEQUENCE: 61 atg gac tgg acc tgg agg gtc ttc tgc ttg ctg gct gta gca cca ggt     48
Met Asp Trp Thr Trp Arg Val Phe Cys Leu Leu Ala Val Ala Pro Gly
1               5                   10                  15 gcc cac tcc cag gtc caa ctg gtg cag tct gga gct gag gtg aag aag     96
Ala His Ser Gln Val Gln Leu Val Gln Ser Gly Ala Glu Val Lys Lys
            20                  25                  30 cct ggg tcc tca gtg aag gtg tcc tgc aag gct tct ggc tac act ttc    144
Pro Gly Ser Ser Val Lys Val Ser Cys Lys Ala Ser Gly Tyr Thr Phe
        35                  40                  45 aca acc tac tat ttg cac tgg gtg agg cag gcc cct gga cag gga ctt    192
Thr Thr Tyr Tyr Leu His Trp Val Arg Gln Ala Pro Gly Gln Gly Leu
    50                  55                  60 gag tgg atg gga tgg att tat cct gga aat gtt cat gct cag tac aat    240
Glu Trp Met Gly Trp Ile Tyr Pro Gly Asn Val His Ala Gln Tyr Asn
65                  70                  75                  80 gag aag ttc aag ggc agg gtc aca atc act gca gac aaa tcc acc agc    288
Glu Lys Phe Lys Gly Arg Val Thr Ile Thr Ala Asp Lys Ser Thr Ser
                85                  90                  95
```

```
aca gcc tac atg gag ctc agc agc ctg agg tct gaa gat act gcg gtc    336
Thr Ala Tyr Met Glu Leu Ser Ser Leu Arg Ser Glu Asp Thr Ala Val
            100                 105                 110 tat tac tgt gca aga tcc tgg gaa ggt ttt cct tac tgg ggc caa ggg    384
Tyr Tyr Cys Ala Arg Ser Trp Glu Gly Phe Pro Tyr Trp Gly Gln Gly
                115                 120                 125 acc acg gtc acc gtc tcc tca gcc tcc acc aag ggc cca tcg gtc ttc    432
Thr Thr Val Thr Val Ser Ser Ala Ser Thr Lys Gly Pro Ser Val Phe
        130                 135                 140 ccc ctg gca ccc tcc tcc aag agc acc tct ggg ggc aca gcg gcc ctg    480
Pro Leu Ala Pro Ser Ser Lys Ser Thr Ser Gly Gly Thr Ala Ala Leu
145                 150                 155                 160 ggc tgc ctg gtc aag gac tac ttc ccc gaa ccg gtg acg gtg tcg tgg    528
Gly Cys Leu Val Lys Asp Tyr Phe Pro Glu Pro Val Thr Val Ser Trp
                165                 170                 175 aac tca ggc gcc ctg acc agc ggc gtg cac acc ttc ccg gct gtc cta    576
Asn Ser Gly Ala Leu Thr Ser Gly Val His Thr Phe Pro Ala Val Leu
            180                 185                 190 cag tcc tca gga ctc tac tcc ctc agc agc gtg gtg acc gtg ccc tcc    624
Gln Ser Ser Gly Leu Tyr Ser Leu Ser Ser Val Val Thr Val Pro Ser
        195                 200                 205 agc agc ttg ggc acc cag acc tac atc tgc aac gtg aat cac aag ccc    672
Ser Ser Leu Gly Thr Gln Thr Tyr Ile Cys Asn Val Asn His Lys Pro
    210                 215                 220 agc aac acc aag gtg gac aag aaa gtt gag ccc aaa tct tgt gac aag    720
Ser Asn Thr Lys Val Asp Lys Lys Val Glu Pro Lys Ser Cys Asp Lys
225                 230                 235                 240 act cac aca tgc cca ccg tgc cca gca cct gaa ctc ctg ggg gga ccg    768
Thr His Thr Cys Pro Pro Cys Pro Ala Pro Glu Leu Leu Gly Gly Pro
                245                 250                 255 tca gtc ttc ctc ttc ccc cca aaa ccc aag gac acc ctc atg atc tcc    816
Ser Val Phe Leu Phe Pro Pro Lys Pro Lys Asp Thr Leu Met Ile Ser
            260                 265                 270 cgg acc cct gag gtc aca tgc gtg gtg gtg gac gtg agc cac gaa gac    864
Arg Thr Pro Glu Val Thr Cys Val Val Val Asp Val Ser His Glu Asp
        275                 280                 285 cct gag gtc aag ttc aac tgg tac gtg gac ggc gtg gag gtg cat aat    912
Pro Glu Val Lys Phe Asn Trp Tyr Val Asp Gly Val Glu Val His Asn
    290                 295                 300 gcc aag aca aag ccg cgg gag gag cag tac aac agc acg tac cgt gtg    960
Ala Lys Thr Lys Pro Arg Glu Glu Gln Tyr Asn Ser Thr Tyr Arg Val
305                 310                 315                 320 gtc agc gtc ctc acc gtc ctg cac cag gac tgg ctg aat ggc aag gag   1008
Val Ser Val Leu Thr Val Leu His Gln Asp Trp Leu Asn Gly Lys Glu
                325                 330                 335 tac aag tgc aag gtc tcc aac aaa gcc ctc cca gcc ccc atc gag aaa   1056
Tyr Lys Cys Lys Val Ser Asn Lys Ala Leu Pro Ala Pro Ile Glu Lys
            340                 345                 350 acc atc tcc aaa gcc aaa ggg cag ccc cga gaa cca cag gtg tac acc   1104
Thr Ile Ser Lys Ala Lys Gly Gln Pro Arg Glu Pro Gln Val Tyr Thr
        355                 360                 365 ctg ccc cca tcc cgg gat gag ctg acc aag aac cag gtc agc ctg acc   1152
Leu Pro Pro Ser Arg Asp Glu Leu Thr Lys Asn Gln Val Ser Leu Thr
    370                 375                 380 tgc ctg gtc aaa ggc ttc tat ccc agc gac atc gcc gtg gag tgg gag   1200
Cys Leu Val Lys Gly Phe Tyr Pro Ser Asp Ile Ala Val Glu Trp Glu
385                 390                 395                 400 agc aat ggg cag ccg gag aac aac tac aag acc acg cct ccc gtg ttg   1248
Ser Asn Gly Gln Pro Glu Asn Asn Tyr Lys Thr Thr Pro Pro Val Leu
```

```
                    405                 410                 415
gac tcc gac ggc tcc ttc ttc ctc tac agc aag ctc acc gtg gac aag        1296
Asp Ser Asp Gly Ser Phe Phe Leu Tyr Ser Lys Leu Thr Val Asp Lys
                420                 425                 430 agc agg tgg cag cag ggg aac gtc ttc tca tgc tcc gtg atg cat gag        1344
Ser Arg Trp Gln Gln Gly Asn Val Phe Ser Cys Ser Val Met His Glu
                435                 440                 445 gct ctg cac aac cac tac acg cag aag agc ctc tcc ctg tct ccc ggt        1392
Ala Leu His Asn His Tyr Thr Gln Lys Ser Leu Ser Leu Ser Pro Gly
                450                 455                 460

<210> SEQ ID NO 62
<211> LENGTH: 464
<212> TYPE: PRT
<213> ORGANISM: Artificial Sequence
<220> FEATURE:
<223> OTHER INFORMATION: Humanized BHA10, heavy chain, version # 3

<400> SEQUENCE: 62

Met Asp Trp Thr Trp Arg Val Phe Cys Leu Leu Ala Val Ala Pro Gly
 1               5                  10                  15

Ala His Ser Gln Val Gln Leu Val Gln Ser Gly Ala Glu Val Lys Lys
                20                  25                  30

Pro Gly Ser Ser Val Lys Val Ser Cys Lys Ala Ser Gly Tyr Thr Phe
            35                  40                  45

Thr Thr Tyr Tyr Leu His Trp Val Arg Gln Ala Pro Gly Gln Gly Leu
        50                  55                  60

Glu Trp Met Gly Trp Ile Tyr Pro Gly Asn Val His Ala Gln Tyr Asn
 65                 70                  75                  80

Glu Lys Phe Lys Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Ser Trp Glu Gly Phe Pro Tyr Trp Gly Gln Gly
        115                 120                 125

Thr Thr Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285
```

-continued

```
Pro Glu Val Lys Phe Asn Trp Tyr Val Asp Gly Val Glu Val His Asn
    290             295             300
Ala Lys Thr Lys Pro Arg Glu Glu Gln Tyr Asn Ser Thr Tyr Arg Val
305             310             315             320
Val Ser Val Leu Thr Val Leu His Gln Asp Trp Leu Asn Gly Lys Glu
                325             330             335
Tyr Lys Cys Lys Val Ser Asn Lys Ala Leu Pro Ala Pro Ile Glu Lys
            340             345             350
Thr Ile Ser Lys Ala Lys Gly Gln Pro Arg Glu Pro Gln Val Tyr Thr
        355             360             365
Leu Pro Pro Ser Arg Asp Glu Leu Thr Lys Asn Gln Val Ser Leu Thr
    370             375             380
Cys Leu Val Lys Gly Phe Tyr Pro Ser Asp Ile Ala Val Glu Trp Glu
385             390             395             400
Ser Asn Gly Gln Pro Glu Asn Asn Tyr Lys Thr Thr Pro Pro Val Leu
                405             410             415
Asp Ser Asp Gly Ser Phe Phe Leu Tyr Ser Lys Leu Thr Val Asp Lys
            420             425             430
Ser Arg Trp Gln Gln Gly Asn Val Phe Ser Cys Ser Val Met His Glu
        435             440             445
Ala Leu His Asn His Tyr Thr Gln Lys Ser Leu Ser Leu Ser Pro Gly
    450             455             460
```

HUMANIZED ANTI-LYMPHOTOXIN BETA RECEPTOR ANTIBODIES

RELATED APPLICATIONS

This application is a continuation of PCT/US03/20762, filed Jul. 1, 2003, which claims the benefit of U.S. Provisional Application No. 60/392,993, filed on Jul. 1, 2002, and to U.S. Provisional Application No. 60/417,372, filed on Oct. 9, 2002. The entire contents of the above-referenced applications are incorporated herein by reference.

FIELD OF THE INVENTION

This invention is in the fields of immunology and cancer diagnosis and therapy. More particularly it concerns humanized antibodies specific for the lymphotoxin beta receptor (LT-β-R), cell lines that produce these antibodies, immunochemicals made from the antibodies, and diagnostic methods that use the antibodies. The invention also relates to the use of the antibodies alone or in combination with chemotherapeutic agent(s) in therapeutic methods.

BACKGROUND OF THE INVENTION

Lymphotoxin beta receptor (referred to herein as LT-β-R) is a member of the tumor necrosis factor family which has a well-described role both in the development of the immune system and in the functional maintenance of a number of cells in the immune system including follicular dendritic cells and a number of stromal cell types (Matsumoto et al., *Immunol. Rev.* 156:137 (1997). Known ligands to the LT-β-R include LTα1/β2 and a second ligand called LIGHT (Mauri et al. *Immunity* 8:21 (1998)). Activation of LT-β-R has been shown to induce the apoptotic death of certain cancer cell lines in vivo (PCT/US96/01386). Treatment with specific humanized anti-LT-β-R antibodies that bind to LT-β-R and has minimal immunogenicity to its subjects, would thus be useful for treating or reducing the advancement, severity or effects of neoplasia in subjects (e.g., humans).

SUMMARY OF THE INVENTION

The present invention provides for humanized antibodies specific for the lymphotoxin beta receptor (LT-β-R), cell lines that produce these antibodies, immunochemicals made from the antibodies, and diagnostic methods that use the antibodies. The invention also relates to the use of the antibodies alone or in combination with chemotherapeutic agent(s) in therapeutic methods. Specifically, the invention embraces a humanized antibody that specifically binds to LT-β-R (e.g., human LT-β-R). This antibody comprises light chain complementary determining regions defined by amino acid residues 24 to 34, 50 to 56 and 89 to 97 of SEQ ID NO: 1, and/or heavy chain complementary determining regions defined by amino acid residues 31 to 35, 50 to 65 and 95 to 102 of SEQ ID NO: 2 and in addition at least one (e.g., 1, 2, 3 or 4) of the following residues in its light chain: Y36, S49, T63 and F87; or at least one (e.g. 1, 2, 3, 4, 5 or 6) of the following residues in its heavy chain: Y27, T30, I48, A67, L69 and F91 (Kabat numbering convention). In another embodiment the invention includes an antibody that binds to the same epitope of LT-β-R as the antibodies listed above.

In one embodiment, a humanized antibody of this invention comprises a light chain variable domain sequence defined by amino acid residues 1 to 107 of SEQ ID NO:6 and/or a heavy chain variable domain sequence defined by amino acid residues 1 to 113 of SEQ ID NO: 14. The humanized antibody may also comprise the same heavy and/or light chain polypeptide sequences as an antibody produced by the CHO cell line expressing version 4 huBHA10: "Clone 3D9" (ATCC patent deposit designation PTA-4726, deposited on Sep. 27, 2002), as described in Example 7. Clone 3D9 containing version 4 huBHA10 was deposited with the American Type Culture Collection (ATCC), 10801 University Boulevard, Manassas, Va. 20110-2209, on Sep. 27, 2002 and assigned Accession Number PTA-4726. This deposit will be maintained under the terms of the Budapest Treaty on the International Recognition of the Deposit of Microorganisms for the Purposes of Patent Procedure. This deposit was made merely as a convenience for those of skill in the art. All restrictions on the availability to the public of the above ATCC deposits will be irrevocably removed upon the granting of a patent on this application.

In another embodiment, the humanized antibody of this invention substantially retains the binding properties of the parent antibody, e.g., the mouse monoclonal antibody BHA10 (described in WO 96/22788). In one embodiment the humanized antibody of this invention binds to LT-β-R with a functional affinity, for example, of about 1 pM to about 10 pM, alternatively, about 10 pM to about 20 pM, alternatively, about 20 pM to about 30 pM, alternatively, about 30 pM to about 40 pM alternatively, about 40 pM to about 50 pM, alternatively, about 50 pM to about 60 pM, alternatively, about 60 pM to about 70 pM, alternatively, about 70 pM to about 80 pM, and alternatively, about 80 pM to about 90 pM, wherein the functional affinity is measured by BIACORE (i.e., surface plasmon resonance using unlabelled reagents), or competitive binding assays In another embodiment, the humanized antibody of this invention is linked to a cytotoxic moiety or toxin e.g., ricin A chain or *Pseudonomas* toxin, in the form of an immunotoxin. The humanized antibody of this invention can also be linked to a chemotherapeutic drug (e.g., Adriamycin, 5FU, Vinblastine, Actinomycin D, Etoposide, Cisplatin, Methotrexate and Doxorubicin). Alternatively, antibodies of the invention can be detectably labeled (e.g., linked to a detectable moiety, such as, for example, a radioisotope). The present invention also embraces a combination therapy in which, for example, the humanized antibody of the present invention which is linked to an a cytotoxic moiety or toxin is used in combination with a humanized antibody of the present invention which is linked to a chemotherapeutic drug. The present invention further embraces a composition suitable for administration to a mammal (e.g., human) having a tumor that expresses LTβR comprising a) a humanized anti-LTβR antibody either alone or in the form of an immunotoxin or a chemotherapeutic drug and b) a cytotoxic factor, each present in amounts effective to reduce tumor volume upon administration to the mammal. The cytotoxic factor may include, for example, TNF-α, TNF-β, IL-1, INF-γ, IL-2. Alternatively, the cytotoxic factor may be a chemotherapeutic drug. The chemotherapeutic drug may include for example, Adriamycin, 5-FU, Vinblastine, Actinomycin D, Etoposide, Cisplatin, Methotrexate and Doxorubicin.

The antibody of this invention can be, in one embodiment, a whole antibody (e.g., with two full length light chains and two full length heavy chains) of any isotype and subtype (e.g., IgM, IgD, IgG1, IgG2, IgG3, IgG4, IgE, IgA1 and IgA2); alternatively, it can be an antigen-binding fragment (e.g., Fab, F(ab')₂, and Fv) of a whole antibody.

Embraced in this invention are also a composition comprising a pharmaceutically acceptable carrier; an isolated nucleic acid comprising a coding sequence for SEQ ID NO:5;

an isolated nucleic acid comprising a coding sequence for SEQ ID NO:13; an isolated nucleic acid comprising a coding sequence for the light chain of an antibody produced by cell line Clone 3D9 (ATCC patent deposit designation PTA-4726, deposited on Sep. 27, 2002); an isolated nucleic acid comprising a coding sequence for the heavy chain of an antibody produced by cell line: Clone 3D9 (ATCC patent deposit designation PTA-4726, deposited on Sep. 27, 2002); an isolated nucleic acid comprising a coding sequence for residues 1-107 of SEQ ID NO:5; and an isolated nucleic acid comprising a coding sequence for residues 1-120 of SEQ ID NO:13.

Embraced within the present invention are also cells from cell lines that produce humanized anti-LTβR antibody, included, for example, cell line: Clone 3D9 (ATCC patent deposit designation PTA-4726). In one embodiment the cell line produces from about 250 mg/L to about 300 mg/L of said antibody, alternatively, the cell line produces from about 300 mg/L to about 350 mg/L of said antibody, alternatively, the cell line produces from about 350 mg/L to about 400 mg/L of said antibody, alternatively, the cell line produces from about 400 mg/L to about 450 mg/L of said antibody, alternatively, the cell line produces from about 450 mg/L to about 500 mg/L of said antibody, alternatively, the cell line produces from about 500 mg/L to about 550 mg/L of said antibody and alternatively, the cell line produces from about 550 mg/L to about 600 mg/L of said antibody. The concentration of the antibody produced by the cell lines is measures as a harvest titer from a 10 day fed batch culture.

The present invention also provides a method of treating or reducing the advancement, severity or effects of neoplasia in a subject (e.g., human) comprising administering to the subject an effective amount of an antibody of this invention. An effective amount of the composition can be administered in one or more dosages. In another embodiment the present invention provides a method of treating or reducing the advancement, severity or effects of neoplasia in a subject (e.g., human) comprising administering to the subject an effective amount of an antibody of this invention and a cytotoxic factor. The cytotoxic factor may include for example, TNF-α, TNF-β, IL-1, INF-γ, IL-2. Alternatively, the cytotoxic factor may by a chemotherapeutic drug. The chemotherapeutic drug includes, for example, Adriamycin, 5-FU, Vinblastine, Actinomycin D, Etoposide, Cisplatin, Methotrexate, DM1 and Doxorubicin.

The invention also describes antigen-binding fragments of the antibodies described herein. In one embodiment of the invention, the fragment is selected from the group consisting of a Fab fragment, a Fab' fragment, a F(ab)$_2$ fragment, and a F$_v$ fragment.

In another embodiment, the antibody or antigen-binding fragment of the invention is conjugated to polyethylene glycol or albumen. In yet another embodiment, the constant region of the antibody of the invention is modified to reduce at least one constant region-mediated biological effector function relative to an unmodified antibody. In still another embodiment, the antibody or antigen-binding fragment of the invention comprises a Fc region having an altered effector function, The invention also describes a hybridoma cell consisting of 3D9 (ATCC Accession No. PTA-4726). In one embodiment, the hybridoma cell of the invention, produces a humanized antibody, or antigen-binding portion thereof.

In another embodiment, the invention provides a light chain comprising the complementarity determining regions (CDRs) and variable region framework amino acid residues Y36, S49, and F87 (Kabat numbering system) from the monoclonal antibody BHA10, wherein the remainder of the light chain is from a human antibody. In still another embodiment, the invention provides a heavy chain comprising the complementarity determining regions (CDRs) and variable region framework amino acid residues Y27 and T30 (Kabat numbering system) from the monoclonal antibody BHA10, wherein the remainder of the heavy chain is from a human antibody. In yet another embodiment, the humanized antibody of the invention comprises said heavy chain and light chains.

In one embodiment, the humanized antibody of the invention binds to lymphotoxin-β receptor (LT-β-R).

The invention also provides a humanized antibody comprising the CDRs of the BHA10 variable light chain sequence set forth as SEQ ID NO: 1. In another embodiment, the invention provides a humanized antibody comprising the CDRs of the BHA10 variable heavy chain sequence set forth as SEQ ID NO: 2.

The invention describes a humanized antibody, or antigen-binding fragment thereof, which specifically binds LT-β-R, comprising a variable region comprising CDRs corresponding to CDRs from the mouse BHA10 antibody. In one embodiment, the fragment is a Fab fragment.

In yet another embodiment, the invention describes a method of treating or reducing cancer in a patient, comprising administering to the patient an effective dosage of the humanized antibody of the invention. The invention also describes a method of treating or reducing a solid tumor in a patient, comprising administering to the patient an effective dosage of the humanized antibody of the invention. In one embodiment of the invention, the solid tumor is selected from the group consisting of non small cell lung cancer (NSCLC), colorectal cancer (CRC), breast cancer, prostate cancer, gastric cancer, skin cancer, stomach cancer, esophagus cancer, and bladder cancer.

BRIEF DESCRIPTION OF THE DRAWINGS

FIG. 4(A) shows the nucleic acid sequence encoding the Light Chain #2 (variable region—single underline; constant region—double underline) (SEQ ID NO:59) and FIG. 4(B) shows the corresponding amino acid sequence (variable region—single underline; constant region—double underline) (SEQ ID NO: 60).

FIG. 6(A) shows the nucleic acid sequence encoding the heavy chain #3 (variable region—single underline; constant region—double underline) (SEQ ID NO: 61) and FIG. 6(B) shows the corresponding amino acid sequence (variable region—single underline; constant region—double underline) (SEQ ID NO: 62).

DETAILED DESCRIPTION

Sequence Identification Numbers

Figure 1:
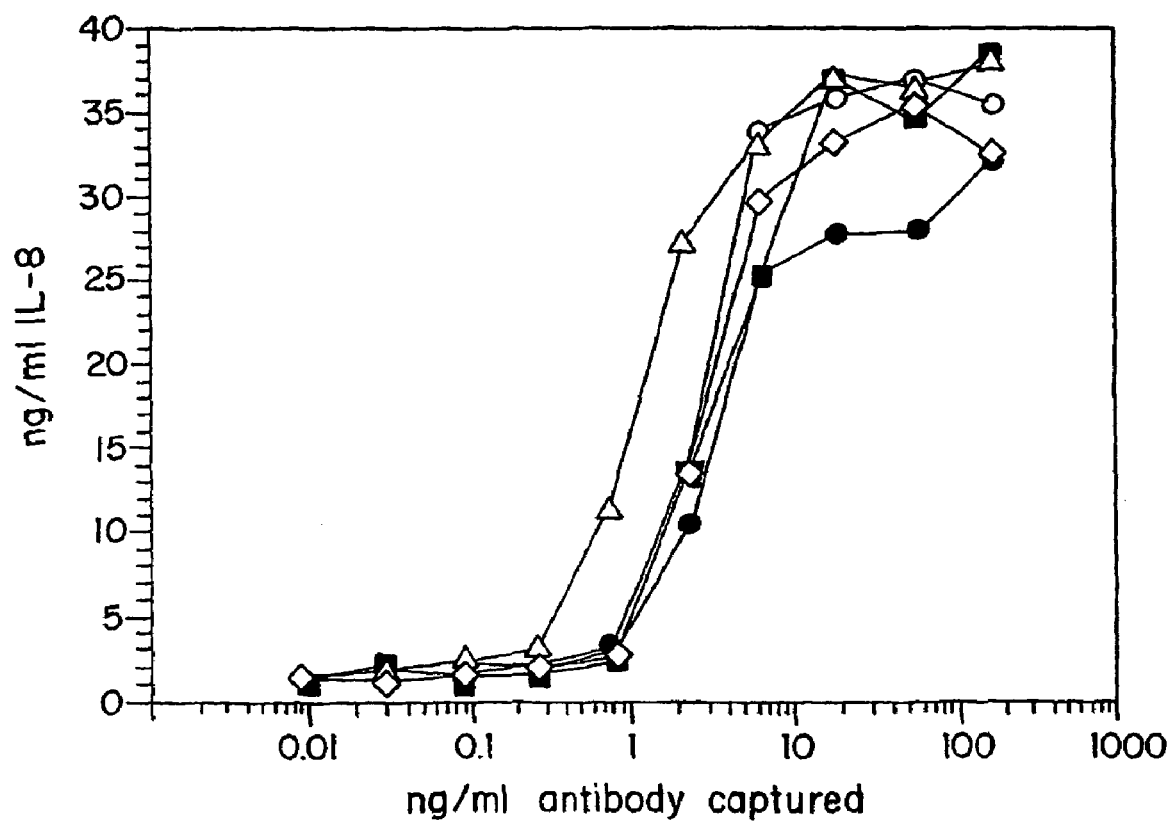
FIG. 1 shows a comparison of different versions of huBHA10 (Versions 2-4) for IL-8 agonism on A375 cells. The IL-8 assay was carried out as described in Example 5. Closed square: chimeric BHA10; open circles: Version 2; closed circles: Version 3; open diamond: Version 4; open triangle: huCBE11 (positive control).

Nucleotide and amino acid sequences referred to in the specification have been given the following sequence identification numbers:

SEQ ID NO:1—Amino acid sequence of murine BHA10 light chain variable (VH) domain.
SEQ ID NO:2—Amino acid sequence of murine BHA10 heavy chain variable (VL) domain.
SEQ ID NO:3—Nucleic acid sequence of humanized BHA10 light chain variable domain (version 1-VL#1).
SEQ ID NO:4—Amino acid sequence of humanized BHA10 light chain variable domain (version 1-VL# 1).
SEQ ID NO:5—Nucleic acid sequence of humanized BHA10 light chain variable domain (version 2-VL#2).
SEQ ID NO:6—Amino acid sequence of humanized BHA10 light chain variable domain (version 2-VL#2)
SEQ ID NO:7—Nucleic acid sequence of humanized BHA10 light chain variable domain (version 3-VL#3).
SEQ ID NO:8—Amino acid sequence of humanized BHA10 light chain variable domain (version 3-VL#3)
SEQ ID NO:9—Nucleic acid sequence of humanized BHA10 heavy chain variable domain (version 1-VH# 1)
SEQ ID NO:10—Amino acid sequence of humanized BHA10 heavy chain variable domain (version 1-VH# 1)
SEQ ID NO:11—Nucleic acid sequence of humanized BHA10 heavy chain variable domain (version 2-VH#2)
SEQ ID NO:12—Amino acid sequence of humanized BHA10 heavy chain variable domain (version 2-VH#2)
SEQ ID NO:13—Nucleic acid sequence of humanized BHA10 heavy chain variable domain (version 3-VH#3)
SEQ ID NO:14—Amino acid sequence of humanized BHA10 heavy chain variable domain (version 3-VH#3)
SEQ ID NO:15—Amino acid sequence of light chain #2 (which includes VL#2 plus light constant domain human kappa).
SEQ ID NO:16—Amino acid sequence of heavy chain #3 (which includes VH#3 plus heavy constant domain human IgG1).
SEQ ID NO:17 to SEQ ID NO:58—various primers.
SEQ ID NO: 59—Nucleic acid sequence of light chain #2 (which includes VL#2 plus light constant domain human kappa) plus start codon and signal sequence.
SEQ ID NO: 60—Amino acid sequence of light chain #2 (which includes VL#2 plus light constant domain human kappa) plus start codon and signal sequence.
SEQ ID NO: 61—Nucleic acid sequence of heavy chain #3 (which includes VH#3 plus heavy constant domain human IgG1) plus start codon and signal sequence.
SEQ ID NO: 62—Amino acid sequence of heavy chain #3 (which includes VH#3 plus heavy constant domain human IgG1) plus start codon and signal sequence.

Definitions

The terms "humanized antibody" or "reshaped antibody," as used interchangeably herein, refer to an antibody that includes at least one humanized immunoglobulin or antibody chain (i.e., at least one humanized light or heavy chain) derived from a non-human parent antibody, typically murine, that retains or substantially retains the antigen-binding properties of the parent antibody but which is preferably less immunogenic in humans. The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain).

The term "region" can refer to a part or portion of an antibody chain or antibody chain domain (e.g., a part or portion of a heavy or light chain or a part or portion of a constant or variable domain, as defined herein), as well as more discrete parts or portions of said chains or domains. For example, light and heavy chains or light and heavy chain variable domains include "complementarity determining regions" or "CDRs" interspersed among "framework regions" or "FRs", as defined herein.

The term complementarity determining region (CDR), as used herein, refers to amino acid sequences which together define the binding affinity and specificity of the natural Fv region of a native immunoglobulin binding site as delineated by Kabat et al., Sequence of Proteins of Immunological Interest, 5$^{th}$ Edition, The United States Department of Health and Human Services, The United States Government Printing Office, 1991.

The term framework region (FR), as used herein, refers to amino acid sequences interposed between CDRs. These portions of the antibody serve to hold the CDRs in appropriate orientation (allows for CDRs to bind antigen).

The term constant region (CR) as used herein, refers to the portion of the antibody molecule which confers effector functions. Typically non-human (e.g., murine), constant regions are substituted by human constant regions. The constant regions of the subject chimeric or humanized antibodies are typically derived from human immunoglobulins. The heavy chain constant region can be selected from any of the five isotypes: alpha, delta, epsilon, gamma or mu. Further, heavy chains of various subclasses (such as the IgG subclasses of heavy chains) are responsible for different effector functions and thus, by choosing the desired heavy chain constant region, antibodies with desired effector function can be produced. Preferred constant regions are gamma 1 (IgG1), gamma 3 (IgG3) and gamma 4 (IgG4). More preferred is an Fc region of the gamma 1 (IgG1) isotype. The light chain constant region can be of the kappa or lambda type, preferably of the kappa type. In one embodiment the light chain constant region is the human kappa constant chain (Heiter et al. (1980) *Cell* 22:197-207) and the heavy constant chain is the human IgG1 constant chain (Ellison et al. (1982) *Nucleic Acids Res.* 10:4076-4079).

The term chimeric antibody as used herein refers to an antibody containing variable regions derived from a first species and containing constant regions derived from a second species. Typically chimeric antibodies comprise human and murine antibody fragments, generally human constant and murine variable region.

Immunoglobulins or antibodies can exist in monomeric or polymeric form, for example, IgM antibodies which exist in pentameric form and/or IgA antibodies which exist in monomeric, dimeric or multimeric form. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc and/or Fv fragments. The term "antigen-binding fragment" refers to a polypeptide fragment of an immunoglobulin or antibody that binds antigen or competes with intact antibody (i.e., with the intact antibody from which they were derived) for antigen binding (i.e., specific binding).

Binding fragments are produced by recombinant DNA techniques, or by enzymatic or chemical cleavage of intact immunoglobulins. Binding fragments include Fab, Fab', F(ab')$_2$, Fabc, Fv, single chains, and single-chain antibodies. Other than "bispecific" or "bifunctional" immunoglobulins or antibodies, an immunoglobulin or antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term immunogenicity as used herein refers to a measure of the ability of a targeting protein or therapeutic moiety to elicit an immune response (humoral or cellular) when administered to a recipient. The present invention is concerned with the immunogenicity of the subject humanized antibodies.

Humanized antibody of reduced immunogenicity refers to a humanized antibody exhibiting reduced immunogenicity relative to the parent antibody, e.g., the murine antibody.

Humanized antibody substantially retaining the binding properties of the parent antibody refers to a humanized antibody which retains the ability to specifically bind the antigen recognized by the parent antibody used to produce such humanized antibody. Preferably the humanized antibody will exhibit the same or substantially the same antigen-binding affinity and avidity as the parent antibody. Ideally, the affinity of the antibody will not be less than 10% of the parent antibody affinity, more preferably not less than about 30%, and most preferably the affinity will not be less than 50% of the parent antibody. Methods for assaying antigen-binding affinity are well known in the art and include half-maximal binding assays, competition assays, and Scatchard analysis. Suitable antigen binding assays are described in this application.

A "back mutation" is a mutation introduced in a nucleotide sequence which encodes a humanized antibody, the mutation results in an amino acid corresponding to an amino acid in the parent antibody (e.g., donor antibody, for example, a murine antibody). Certain framework residues from the parent antibody may be retained during the humanization of the antibodies of the invention in order to substantially retain the binding properties of the parent antibody, while at the same time minimizing the potential immunogenicity of the resultant antibody. In one embodiment of the invention, the parent antibody is of mouse origin. For example, the back mutation changes a human framework residue to a parent murine residue. Examples of framework residues that may be back mutated include, but are not limited to, canonical residues, interface packing residues, unusual parent residues which are close to the binding site, residues in the "Vernier Zone" (which forms a platform on which the CDRs rest) (Foote & Winter, 1992, *J. Mol. Biol.* 224, 487-499), and those close to CDR H3.

As used herein a "conservative change" refers to alterations that are substantially conformationally or antigenically neutral, producing minimal changes in the tertiary structure of the mutant polypeptides, or producing minimal changes in the antigenic determinants of the mutant polypeptides, respectively, as compared to the native protein. When referring to the antibodies and antibody fragments of the invention, a conservative change means an amino acid substitution that does not render the antibody incapable of binding to the subject receptor. Those of ordinary skill in the art will be able to predict which amino acid substitutions can be made while maintaining a high probability of being conformationally and antigenically neutral. Such guidance is provided, for example in Berzofsky, (1985) *Science* 229:932-940 and Bowie et al. (1990) *Science* 247:1306-1310. Factors to be considered that affect the probability of maintaining conformational and antigenic neutrality include, but are not limited to: (a) substitution of hydrophobic amino acids is less likely to affect antigenicity because hydrophobic residues are more likely to be located in a protein's interior; (b) substitution of physiochemically similar, amino acids is less likely to affect conformation because the substituted amino acid structurally mimics the native amino acid; and (c) alteration of evolutionarily conserved sequences is likely to adversely affect conformation as such conservation suggests that the amino acid sequences may have functional importance. One of ordinary skill in the art will be able to assess alterations in protein conformation using well-known assays, such as, but not limited to micro-complement fixation methods (Wasserman et al. (1961) J. Immunol. 87:290-295; Levine et al. (1967) Meth. Enzymol. 11:928-936) and through binding studies using conformation-dependent monoclonal antibodies (Lewis et al. (1983) Biochem. 22:948-954).

As used herein, "therapeutic composition" refers to a composition which directly or indirectly ameliorates a disease condition. That is, administration of the composition alleviates at least one symptom of a disease or disorder.

The term "specific for," when used to describe antibodies of the invention, indicates that the variable regions of the antibodies of the invention recognize and bind a set of one or more receptors (i.e., are able to distinguish LT-β-RS from other polypeptides by virtue of measurable differences in binding affinity, despite the possible existence of localized sequence identity, homology, or similarity between LT-β-R and such polypeptides). It will be understood that specific antibodies may also interact with other proteins (for example, *Staphylococcus aureus* protein A or other antibodies in ELISA techniques) through interactions with sequences outside the variable region of the antibodies, and, in particular, in the constant region of the molecule. Screening assays to determine binding specificity of an antibody of the invention are well known and routinely practiced in the art. For a comprehensive discussion of such assays, see Harlow et al. (Eds.), ANTIBODIES: A LABORATORY MANUAL; Cold Spring Harbor Laboratory; Cold Spring Harbor, N.Y., 1988, Chapter 6. Antibodies that recognize and bind fragments of the LT-β R are also contemplated, provided that the antibodies are specific for LT-β-RS. Antibodies of the invention can be produced using any method well known and routinely practiced in the art.

The term "monoclonal antibody" or "monoclonal antibody composition," as used herein, refers to a population of antibody molecules that contain only one species of an antigen-binding site capable of immunoreacting with or binding to a particular epitope of a LT-β-R. A monoclonal antibody composition thus typically displays a single binding affinity for a particular epitope of LT-β-R with which it immunoreacts. For preparation of monoclonal antibodies directed toward LT-β-R, or derivatives, fragments, analogs or homologs thereof, any technique that provides for the production of antibody molecules by continuous cell line culture may be utilized. Such techniques include, but are not limited to, the hybridoma technique (see Kohler & Milstein (1975) *Nature* 256:495-497); the trioma technique; the human B-cell hybridoma technique (see Kozbor, et al. (1983) *Immunol. Today* 4:72) and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized in the practice of the present invention and may be produced by using human hybridomas (see Cote et al. (1983). *Proc. Natl. Acad. Sci. USA* 80: 2026-2030) or by transforming human B-cells with Epstein Barr Virus in vitro (see Cole et al. (1985) In: MONOCLONAL ANTIBODIES AND CANCER THERAPY, Alan R. Liss, Inc., pp. 77-96). The chimeric and humanized monoclonal antibodies of the invention can be produced by recombinant DNA techniques known in the art, for example using methods described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; Shaw et al. (1988) *J. Natl. Cancer Inst.* 80:1553-1559); Morrison (1985) *Science* 229:1202-1207; Oi et al. (1986) *BioTechniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141: 4053-4060.

The present invention is directed to humanized monoclonal antibodies which bind human LT-β-R and diagnostic methods that use the antibodies as well as their use as therapeutic agents. The present invention is further directed toward nucleic acid sequences which encode said humanized antibodies, and their expression in recombinant host cells. More specifically, the present invention is directed toward humanized antibodies derived from murine BHA10 which specifically binds to human LT-β-R.

Murine BHA10 (mBHA10) is a murine IgG1, kappa antibody isolated from a mouse immunized with a human LT-β-R-Ig fusion protein (Browning et al., *J. Immunol.* 154: 33 (1995)). Its isolation and anti-tumor properties have been described (Browning et al. *J. Exp. Med.* 183:867 (1996). The hybridoma cell line which produces mBHA10 has been previously deposited with the American Type Culture Collection (ATCC) according to the provisions of the Budapest Treaty by the Applicants of the present invention and was assigned the ATCC accession number HB 11795. (PCT/US96/01386). Applicants have also shown that LT-β receptor cross-linking with various agonist anti-LT-β-R antibodies activate the LT-β receptor (i.e. can mimic the effects of the natural ligands). (PCT/US96/01386). Receptor activation in turn has been shown to inhibit tumor growth in a variety of in vivo tumor models for which LT-β receptor is expressed. LT-β receptor has been shown to be expressed on a number of cancer cells including for example non small cell lung cancer cells (NSCLC), colorectal cancer cells (CRC), breast cancer cells, as well as on prostate, gastric, skin, stomach, esophageal and bladder cancer cells. Non-limiting examples of tumors that the agonist LT-β-R antibodies inhibit include the following solid tumors: HT29 colon adenocarcinoma, HT3 cervical carcinoma, A375 melanoma, MDA-231 breast carcinoma and primary colon tumors. Therefore, agonist LT-β-R antibodies, particularly humanized antibodies as described herein, possess properties which render them useful for treatment of diseases wherein LT-β-R activation and/or modulation of the LT-β-R/LT-β-R ligand interaction is desirable including for example the treating or reducing the advancement, severity or effects of neoplasia in a subject (e.g., human).

Humanizing the mBHA10 monoclonal antibody including the modeling analysis and back mutations required to substantially retain the binding properties of the mBHA10 monoclonal antibody is described herein.

Modeling Analysis of the Mouse Variable Regions:

The CDRs contain the residues most likely to bind antigen and must be retained in the reshaped antibody. CDRs are defined by sequence according to Kabat et al., Sequence of Proteins of Immunological Interest, 5th Edition, The United States Department of Health and Human Services, The United States Government Printing Office, 1991. CDRs fall into canonical classes (Chothia et al, 1989 *Nature,* 342, 877-883) where key residues determine to a large extent the structural conformation of the CDR loop. These residues are almost always retained in the reshaped antibody. The polypeptide sequence of the light chain variable domain of mBHA10 is shown below with the CDR's underlined and the residue position numbers are designated according with the Kabat numbering system:

```
 1 DIVMTQSQKF MSTSVGDRVS VTCKASQNVG INVAWYQQKP   (SEQ ID NO:1)
41 GQSPKSLISS ASYRYSGVPD RFTGSGSGTD FTLTITNVQS
81 EDLAEYFCQQ YDTYPFTFGS GTKLEIK
```

The polypeptide sequence of the heavy chain variable domain of mBHA10 is shown below with the CDR's underlined and the residue position number are designated according with the Kabat numbering system (which includes bolded amino acids 52a (pro), 82a (ser), 82b (ser), 82c (leu) and no amino acid at position 100):

```
  1 QVQLQQSGPE LVKPGASVRI SCKASGYTFT TYYLHWVKQR   (SEQ ID NO:2)

aa52a
 41 PGQGLEWIGW IYPGNVHAQYN EKFKGKATLT ADKSSSTAYM aa82a-82c                aa100
 81 QLSSLTSEDSAIY FCARSWEGF* PYWGQGTTVT VSS
```

The variable light and heavy chains of mBHA10 were compared with the consensus sequences for mouse and human subgroups (Johnson, G., Wu, T. T. Kabat Database and its applications: future directions *Nucleic Acid Research,* 29, 205-206, 2001; Wu and Kabat, *J. Exp. Med* 132:211-250 (1970)) using the program FASTA. The mBHA10 variable light chain is a member of mouse kappa I with a 63.7% identity over 113 amino acids and the mBHA10 variable heavy chain is a member of mouse subgroup IIb with a 73.2% identity over 127 amino acids. The variable light chain corresponds to human kappa I with a 61.1% identity over 113 amino acids. The variable heavy chain corresponds to human subgroup I with a 62% identity over 129 amino acids.

The complementarity determining regions (CDRs) of the present invention were classified into canonical classes. The L1 loop fell into canonical class 2 (11 residue loop), L2 into class 1 (7 residues) and L3 into class 1 (9 residues). The H1 loop fell into class 1 (5 residues) allowing Leu34. The H2 and H3 loops did not belong to a canonical class. The canonical residues important for these classes are indicated in Table 1 below.

TABLE 1

| | |
|---|---|
| L1 | Class 22(I) 25(A) 29(I) 33(L) 71(Y) |
| L2 | Class 148(I) 51(A) 52(T) 64(G) |
| L3 | Class 190(Q) 95(P) |
| H1 | Class 124(A) 26(G) 27(F) 29(F) 34(M) 94(R) |
| H2 | No canonical class |
| H3 | No canonical class |

The residues at the interface between the variable light and heavy chains have been defined (Chothia et al, 1985 *J. Mol. Biol.,* 186, 651-663). These are usually retained in the reshaped antibody. In mBHA10 several of these residues are unusual at the interface, namely tyrosine 36 and phenylalanine 87 in the variable light chain and phenylalanine 91 in variable heavy chain.

Unusual framework residues were determined by analyzing all mouse and human variable chain sequences in the September 1999 version of the Kabat database [NCBI, NIH]. It is believed that mBHA10-specific differences might indicate somatic mutations that enhance binding activity if these differences were close to the binding site. Unusual framework residues found were Y36, S49, T63 and F87 in the light chain; and Y27, T30, I48, A67, L69 and F91 in the heavy chain.

Modeling the Structure of the Variable Regions

The light and heavy chains of the present invention were aligned against the non-redundant database to determine structural frames to be used to construct three dimensional models of the light and heavy chains. Using BLAST the light chain was found to have 85% sequence identity to murine Fab fragment (12E8), and the heavy chain was found to have 81% sequence identity to murine IGGA2 Fab fragment (1PLGH). Using the molecular modeling package Sybyl (Tripos Inc.) the three dimensional structures of the light and heavy chains were built using the light chain of 12E8 and the heavy chain of 1PLGH, respectively. The structural integrity of the models was assessed at the console and were found to be reasonable.

Design of the Reshaped Variable Regions

Germline matching was used to choose human acceptor frameworks to "accept" the mBHA10 CDRs (Rosok et al. *J. Biol. Chem* (1996) 271:22611-22618). Both the Germline database and the non-redundant database from NCBI, ENTRZ (The National Institutes of Health) were searched using the software program IgBLAST. The choice of human acceptor frameworks was made based on sequence identity and possible back mutations The eventual choice of human frameworks was from germline sequences L1/L15 and J1 (Bentley et al. (1983) *Cell* 32:181-189; Cox et al. (1994) *Eur. J. Immunol.,* 24:827-836 and Heiter et al. (1982) *J. Biol. Chem.* 257:1516-1522) for the variable light (VL) chain and germline sequences 1-69/J6 (Tomlinson et al. (1992) *J. Mol. Biol.,* 227:776-798 and Mattila et al. (1995) *Eur. J. Immunol.,* 25:2578-2582) for the variable heavy (VH) chain. The human VL and VH frameworks have 21 residues differences each compared to the murine sequences.

Back Mutations of the Human Frameworks

The most unpredictable procedure in the humanization of monoclonal antibodies is the identification of critical framework residues from the parent antibody (i.e. in the present case, the parent antibody is of mouse origin) that need to be retained in order to substantially retain the binding properties of the parent antibody while at the same time minimizing the potential immunogenicity of the resultant antibody. It is especially important to retain canonical residues, interface packing residues and unusual murine residues which are close to the binding site. In addition, residues in the 'Vernier Zone' (which forms a platform on which the CDRs rest) (Foote & Winter, 1992 *J. Mol. Biol.* 224, 487-499) and those close to CDR H3 are considered. Mutations back to the parent antibody (i.e. back mutating from human framework residues to mouse) are referred to herein as back mutations.

Three versions of the reshaped variable light chain (VL#) and three versions of the reshaped variable heavy chain (VH#) have been made. In general, the first version contains the most back mutations and the third version contains the fewest (i.e. the most "humanized"). The present invention contemplates humanized antibodies derived from mBHA10 which comprise a variable light chain selected from the variable light chains described below (i.e. VL#1, VL#2 or VL#3) and a variable heavy chain selected from the variable heavy chains described below (i.e. VH#1, VH#2 or VH#3) in any combination.

Back Mutations in the Reshaped Variable Light Chain:

36 F (phenylalanine)->Y (tyrosine) This is a packing residue. It was back mutated from a phenylalanine to a tyrosine in VL# 1 and VL#2 of the variable light chain constructs but retained as a phenylalanine in VL#3 of the variable light chain constructs.

49 Y (tyrosine)->S (serine) This position is close to the CDR and is unusual in both mouse and human frameworks. It was back mutated from a tyrosine to a serine in all three versions of the variable light chain constructs.

63 S (serine)->T (threonine) This position is close to the CDR. It was back mutated from a serine to a threonine in VL#1 of the variable light chain constructs only.

87 Y (tyrosine)->F (phenylalanine) This is a packing residue and is unusual in human frameworks. It was back mutated from a tyrosine to a phenylalanine in VL# 1 and VL#2 of the variable light chain constructs but retained as a tyrosine in VL#3.

Back Mutations in the Reshaped Variable Heavy Chain:

27 G (glycine)->Y (tyrosine). This is a canonical residue which is back mutated to the murine residue in all three versions.

30 S (serine)->T (threonine). This position is close to the CDR and may influence conformation. It was back mutated from a serine to a threonine in all three versions of the variable heavy chain constructs.

48 M (methionine)->I (isoleucine) This position is close to the CDR. It was back mutated from a methionine to an isoleucine in VH#1 and VH#2 of the variable heavy chain constructs but not in VH#3.

67 V (valine)->A (alanine). This position is close to the CDR and is unusual in human frameworks. It was back mutated from a valine to an alanine in VH#1 and VH#2 of the variable heavy chain constructs but not in VH#3.

69 I (isoleucine)->L (leucine). This position is close to the CDR and is unusual in human frameworks. It was back mutated from an isoleucine to a leucine in VH#1 of the variable heavy chain constructs but not in VH#2 and VH#3.

91 Y (tyrosine)->F (phenylalanine). This is a packing residue. It was back mutated from an tyrosine to a phenylalanine in VH#1 of the variable heavy chain constructs but not in VH#2 and VH#3.

The amino acid and nucleic acid sequences of each of the different versions of the variable light and heavy chains are as follows:

Reshaped Variable Light Chains

Reshaped variable light chain of BHA10—variable light chain—version 1 (VL#1):

```
  1 GACATTCAGATGACCCAGTCTCCTAGCTCCCTGTCCGCCTCAGTAGGAGACAGGGTCACC   60
    D I Q M T Q S P S S L S A S V G D R V T

61 ATCACCTGCAAGGCCAGTCAGAATGTGGGTATTAACGTTGCCTGGTATCAACAGAAACCA  120
    I T C K A S Q N V G I N V A W Y Q Q K P
                                                           aa36
121 GGGAAGGCTCCTAAATCACTGATTTCCTCGGCCTCCTACCGGTACAGTGGAGTCCCTTCT  180
    G K A P K S L I S S A S Y R Y S G V P S
                        aa49
181 AGATTCACAGGCAGTGGATCTGGGACAGATTTCACTCTCACCATCAGCAGCCTGCAGCCT  240
    R F T G S G S G T D F T L T I S S L Q P
        aa63
241 GAAGACTTCGCAACCTATTTCTGTCAGCAATATGACACCTATCCATTCACGTTCGGCCAG  300
    E D F A T Y F C Q Q Y D T Y P F T F G Q
                    aa87
301 GGTACCAAGGTGGAGATCAAA                                         321
    G T K V E I K
```

SEQ ID NO:3—represents the nucleic acid sequence of the reshaped VL#1 above.

SEQ ID NO:4—represents the amino acid sequence of the reshaped VL#1 above.

Reshaped variable light chain of BHA10—variable light chain—version 2 (VL#2):

```
  1 GACATTCAGATGACCCAGTCTCCTAGCTCCCTGTCCGCCTCAGTAGGAGACAGGGTCACC   60
    D I Q M T Q S P S S L S A S V G D R V T

61 ATCACCTGCAAGGCCAGTCAGAATGTGGGTATTAATGTAGCCTGGTATCAACAGAAACCA  120
    I T C K A S Q N V G I N V A W Y Q Q K P
                                                           aa36
121 GGGAAGGCTCCTAAATCACTGATTTCCTCGGCCTCCTACCGGTACAGTGGAGTCCCTTCC  180
    G K A P K S L I S S A S Y R Y S G V P S
                        aa49
181 AGATTCAGCGGCAGTGGATCTGGGACAGATTTCACTCTCACCATCAGCAGCCTCCAGCCT  240
    R F S G S G S G T D F T L T I S S L Q P
```

```
241  GAAGACTTCGCAACCTATTTCTGTCAGCAATATGACACCTATCCATTCACGTTCGGCCAG  300
      E  D  F  A  T  Y  F  C  Q  Q  Y  D  T  Y  P  F  T  F  G  Q aa87
301  GGTACCAAGGTGGAGATCAAA                                         321
      G  T  K  V  E  I  K
```

SEQ ID NO:5—represents the nucleic acid sequence of the reshaped VL#2 above.

SEQ ID NO:6—represents the amino acid sequence of the reshaped VL#2 above.

Reshaped variable light chain of BHA10—variable light chain—version 3 (VL#3):

```
  1  GACATTCAGATGACCCAGTCTCCTAGCTCCCTGTCCGCCTCAGTAGGAGACAGGGTCACC   60
      D  I  Q  M  T  Q  S  P  S  S  L  S  A  S  V  G  D  R  V  T

61  ATCACCTGCAAGGCCAGTCAGAATGTGGGTATTAATGTAGCCTGGTTCCAACAGAAACCC  120
      I  T  C  K  A  S  Q  N  V  G  I  N  V  A  W  F  Q  Q  K  P

121  GGGAAGGCTCCTAAATCACTGATTTCCTCGGCCTCCTACCGGTACAGTGGAGTCCCTTCT  180
      G  K  A  P  K  S  L  I  S  S  A  S  Y  R  Y  S  G  V  P  S aa49
181  AGATTCAGCGGCAGTGGATCTGGGACAGATTTCACTCTCACCATCAGCAGCCTGCAGCCT  240
      R  F  S  G  S  G  S  G  T  D  F  T  L  T  I  S  S  L  Q  P

241  GAAGACTTCGCAACCTATTACTGTCAGCAATATGACACCTATCCATTCACGTTCGGCCAG  300
      E  D  F  A  T  Y  Y  C  Q  Q  Y  D  T  Y  P  F  T  F  G  Q

301  GGTACCAAGGTGGAGATCAAA                                         321
      G  T  K  V  E  I  K
```

SEQ ID NO:7—represents the nucleic acid sequence of the reshaped VL#3 above.

SEQ ID NO:8—represents the amino acid sequence of the reshaped VL#3 above.

Reshaped Variable Heavy Chains:

Reshaped variable heavy chain of BHA10—variable heavy chain—version 1 (VH#1)

SEQ ID NO:9—represents the nucleic acid sequence of the reshaped VH#1 above.

SEQ ID NO:10—represents the amino acid sequence of the reshaped VH# 1 above (kabat numbering system which includes a proline at position 52a, serine at position 82a, a serine at position 82b, a leucine at position 82c and a missing amino acid at position 100).

```
  1  CAGGTCCAACTGGTGCAGTCTGGAGCTGAGGTGAAGAAGCCTGGGTCCTCAGTGAAGGTG   60
      Q  V  Q  L  V  Q  S  G  A  E  V  K  K  P  G  S  S  V  K  V

61  TCCTGCAAGGCTTCTGGCTACACTTTCACAACCTACTATTTGCACTGGGTGAGGCAGGCC  120
      S  C  K  A  S  G  Y  T  F  T  T  Y  Y  L  H  W  V  R  Q  A aa27       aa30
121  CCTGGACAGGGACTTGAGTGGATTGGATGGATTTATCCTGGAAATGTTCATGCTCAGTAC  180
      P  G  Q  G  L  E  W  I  G  W  I  Y  P  G  N  V  H  A  Q  Y aa48
181  AATGAGAAGTTCAAGGGCAGGGCCACACTGACAGCAGACAAATCCACCAGCACAGCCTAC  240
      N  E  K  F  K  G  R  A  T  L  T  A  D  K  S  T  S  T  A  Y aa67  aa69
241  ATGGAGCTCAGCAGCCTGAGGTCTGAAGATACTGCGGTCTATTTCTGTGCAAGATCCTGG  300
      M  E  L  S  S  L  R  S  E  D  T  A  V  Y  F  C  A  R  S  W aa91
301  GAAGGTTTTCCTTACTGGGGCCAAGGGACCACGGTCACCGTCTCCTCA              348
      E  G  F  P  Y  W  G  Q  G  T  T  V  T  V  S  S
```

Reshaped variable heavy chain of BHA10—variable heavy chain—version 2 (VH#2)

```
  1  CAGGTCCAACTGGTGCAGTCTGGAGCTGAGGTGAAGAAGCCTGGGTCCTCAGTGAAGGTG   60
     Q  V  Q  L  V  Q  S  G  A  E  V  K  K  P  G  S  S  V  K  V

61  TCCTGCAAGGCTTCTGGCTACACTTTCACAACCTACTATTTGCACTGGGTGAGGCAGGCC  120
     S  C  K  A  S  G  Y  T  F  T  T  Y  Y  L  H  W  V  R  Q  A aa27        aa30
121  CCTGGACAGGGACTTGAGTGGATTGGATGGATTTATCCTGGAAATGTTCATGCTCAGTAC  180
     P  G  Q  G  L  E  W  I  G  W  I  Y  P  G  N  V  H  A  Q  Y aa48
181  AATGAGAAGTTCAAGGGCAGGGCCACAATCACTGCAGACAAATCCACCAGCACAGCCTAC  240
     N  E  K  F  K  G  R  A  T  I  T  A  D  K  S  T  S  T  A  Y aa67
241  ATGGAGCTCAGCAGCCTGAGGTCTGAAGATACTGCGGTCTATTACTGTGCAAGATCCTGG  300
     M  E  L  S  S  L  R  S  E  D  T  A  V  Y  Y  C  A  R  S  W

301  GAAGGTTTTCCTTACTGGGGCCAAGGGACCACGGTCACCGTCTCCTCA              348
     E  G  F  P  Y  W  G  Q  G  T  T  V  T  V  S  S
```

SEQ ID NO:11—represents the nucleic acid sequence of the reshaped VH#2 above.

SEQ ID NO:12—represents the amino acid sequence of the reshaped VH#2 above (kabat numbering system which includes a proline at position 52a, serine at position 82a, a serine at position 82b, a leucine at position 82c and a missing amino acid at position 100).

Reshaped variable heavy chain of BHA10—variable heavy chain—version 3 (VH#3)

```
  1  CAGGTCCAACTGGTGCAGTCTGGAGCTGAGGTGAAGAAGCCTGGGTCCTCAGTGAAGGTG   60
     Q  V  Q  L  V  Q  S  G  A  E  V  K  K  P  G  S  S  V  K  V

61  TCCTGCAAGGCTTCTGGCTACACTTTCACAACCTACTATTTGCACTGGGTGAGGCAGGCC  120
     S  C  K  A  S  G  Y  T  F  T  T  Y  Y  L  H  W  V  R  Q  A aa27        aa30
121  CCTGGACAGGGACTTGAGTGGATGGGATGGATTTATCCTGGAAATGTTCATGCTCAGTAC  180
     P  G  Q  G  L  E  W  M  G  W  I  Y  P  G  N  V  H  A  Q  Y

181  AATGAGAAGTTCAAGGGCAGGGTCACAATCACTGCAGACAAATCCACCAGCACAGCCTAC  240
     N  E  K  F  K  G  R  V  T  I  T  A  D  K  S  T  S  T  A  Y

241  ATGGAGCTCAGCAGCCTGAGGTCTGAAGATACTGCGGTCTATTACTGTGCAAGATCCTGG  300
     M  E  L  S  S  L  R  S  E  D  T  A  V  Y  Y  C  A  R  S  W

301  GAAGGTTTTCCTTACTGGGGCCAAGGGACCACGGTCACCGTCTCCTCA              348
     E  G  F  P  Y  W  G  Q  G  T  T  V  T  V  S  S
```

SEQ ID NO:13—represents the nucleic acid sequence of the reshaped VH#3 above.

SEQ ID NO:14—represents the amino acid sequence of the reshaped VH#3 above (kabat numbering system which includes a proline at position 52a, serine at position 82a, a serine at position 82b, a leucine at position 82c and a missing amino acid at position 100).

Humanized BHA10 antibodies were constructed using the reshaped variable light and heavy chains described above and further described in Example 4. For example, the humanized BHA10 antibody version 4 ("Version 4 huBHA10") was constructed, as described in Example 4, using expression vector pKJS49 which contains Light chain #2 in combination with expression vector pKJS46 which contains Heavy chain #3. The amino acid and nucleic acid sequences of light and heavy chains of Version 4 huBHA10 are listed below:

```
DIQMTQSPSS LSASVGDRVT ITCKASQNVG INVAWYQQKP GKAPKSLISS            (SEQ ID NO: 15)
                                    aa36           aa49
           ASYRYSGVPS RFSGSGSGTD FTLTISSLQP EDFATYFCQQ YDTYPFTFGQ
                                           aa87
           GTKVEIK{RTV AAPSVFIFPP SDEQLKSGTA SVVCLLNNFY PREAKVQWKV DNALQSGNSQ

ESVTEQDSKD STYSLSSTLT LSKADYEKHK VYACEVTHQG LSSPVTKSFN

RGEC}
```

The above SEQ ID NO:15—represents the amino acid sequence of the light chain of Version 4 huBHA10. CDRs are underlined; back mutations Y36, S49 and F87 are bolded; the human kappa constant domain, is bracketed (kabat numbering system)

```
QVQLVQSGAE VKKPGSSVKV SCKASGYTFT TYYLHWVRQA PGQGLEWMGW    (SEQ ID NO: 16)
                            aa27 aa30
IYPGNVHAQY NEKFKGRVTI TADKSTSTAY MELSSLRSED TAVYYCARSWEGF

PYWGQGT TVTVSS {ASTKGPSVFP LAPSSKSTSG GTAALGCLVK

DYFPEPVTVS WNSGALTSGV HTFPAVLQSS GLYSLSSVVT VPSSSLGTQT

YICNVNHKPS NTKVDKKVEP KSCDKTHTCP PCPAPELLGG PSVFLFPPKP

KDTLMISRTP EVTCVVVDVS HEDPEVKFNW YVDGVEVHNA KTKPREEQYN

STYRVVSVLT VLHQDWLNGK EYKCKVSNKA LPAPIEKTIS KAKGQPREPQ

VYTLPPSRDE LTKNQVSLTC LVKGFYPSDI AVEWESNGQP ENNYKTTPPV

LDSDGSFFLY SKLTVDKSRW QQGNVFSCSV MHEALHNHYT QKSLSLSPG}
```

The above SEQ ID NO:16—represents the amino acid sequence of the heavy chain of Version 4 huBHA10. CDRs are underlined; back mutations Y27 and T30 are bolded; human IgG1 constant domain is bracketed (kabat numbering system).

Other humanized antibodies comprising different versions of the reshaped light variable and heavy variable chains described herein can be made. For example, one can made an antibody comprising a human constant light chain (a non-limiting example includes the human kappa constant domain) and human constant heavy chain (a non-limiting example includes the human IgG1 constant domain) in combination with any one of the reshaped variable light chains (VL#1, VL#2 or VL#3) and the reshaped variable heavy chains (VH#1, VH#2 or VH#3).

The invention further contemplates equivalents and variants of the reshaped VH and VL sequences, e.g., those containing one or more conservative amino acid substitutions which do not substantially affect LT-β-R binding. Humanized LT-β-R antibodies containing these humanized variable heavy and light sequences may be obtained by recombinant methods as described in the Examples.

In another embodiment, immunochemical derivatives of the antibodies of this invention are contemplated including for example 1) immunotoxins (conjugates of the antibody and a cytotoxic moiety) and 2) labeled derivatives (i.e. radiolabeled, enzyme-labeled or fluorochrome-labeled) in which the label provides a means for identifying immune complexes that include the labeled antibody.

The cytotoxic moiety may be a cytotoxic drug or an enzymatically active toxin of bacterial or plant origin, or an enzymatically active fragment of such a toxin. Enzymatically active toxins and fragments thereof used are diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolacca americana* proteins (PAPI, PAPII, and PAP-S), *momordica charantia* inhibitor, curcin, crotin, *sapaonaria officinalis* inhibitor, gelonin, mitogellin, restrictocin, phenomycin, and enomycin. Alternatively, the antibodies are conjugated to small molecule anti-cancer drugs.

Conjugates of the monoclonal antibody are made using a variety of bifunctional protein coupling agents. Examples of such reagents are SPDP, IT, bifunctional derivatives of imidoesters such a dimethyl adipimidate HCl, active esters such as disuccinimidyl suberate, aldehydes such as glutaraldehyde, bis-azido compounds such as bis(p-azidobenzoyl)hexanediamine, bis-diazonium derivatives such as bis-(p-diazoniumbenzoyl)-ethylenediamine, diisocyanates such as tolylene 2,6-diisocyanate, and bis-active fluorine compounds such as 1,5-difluoro-2,4-dinitrobenzene. The lysing portion of a toxin may be joined to the Fab fragment of the antibodies.

Cytotoxic radiopharmaceuticals for treating cancer may be made by conjugating radioactive isotopes (e.g. I, Y, Pr) to the antibodies. The term "cytotoxic moiety" as used herein is intended to include such isotopes.

In another embodiment, liposomes are filled with a cytotoxic drug and the liposomes are coated with antibodies specifically binding a growth factor receptor. Since there are many receptor sites, this method permits delivery of large amounts of drug to the correct cell type.

Chemical Modifications

In some embodiments, the antibodies and antibody fragments of the invention may be chemically modified to provide a desired effect. For example, pegylation of antibodies and antibody fragments of the invention may be carried out by any of the pegylation reactions known in the art, as described, for example, in the following references: *Focus on Growth Factors* 3:4-10 (1992); EP 0 154 316; and EP 0 401 384 (each of which is incorporated by reference herein in its entirety). Preferably, the pegylation is carried out via an acylation reaction or an alkylation reaction with a reactive polyethylene glycol molecule (or an analogous reactive water-soluble polymer). A preferred water-soluble polymer for pegylation of the antibodies and antibody fragments of the invention is polyethylene glycol (PEG). As used herein, "polyethylene glycol" is meant to encompass any of the forms of PEG that have been used to derivatize other proteins, such as mono (Cl-ClO) alkoxy- or aryloxy-polyethylene glycol.

Methods for preparing pegylated antibodies and antibody fragments of the invention will generally comprise the steps of (a) reacting the antibody or antibody fragment with polyethylene glycol, such as a reactive ester or aldehyde derivative of PEG, under conditions whereby the antibody or antibody fragment becomes attached to one or more PEG groups, and (b) obtaining the reaction products. It will be apparent to one of ordinary skill in the art to select the optimal reaction conditions or the acylation reactions based on known parameters and the desired result.

Pegylated antibodies and antibody fragments may generally be used to treat conditions that may be alleviated or modulated by administration of the antibodies and antibody fragments described herein. Generally the pegylated antibodies and antibody fragments have increased half-life, as compared to the nonpegylated antibodies and antibody fragments. The pegylated antibodies and antibody fragments may be employed alone, together, or in combination with other pharmaceutical compositions.

In other embodiments of the invention the antibodies or antigen-binding fragments thereof are conjugated to albumen using art recognized techniques.

In another embodiment of the invention, antibodies, or fragments thereof are modified to reduce or eliminate potential glycosylation sites. Such modified antibodies are often referred to as "aglycosylated" antibodies. In order to improve the binding affinity of an antibody or antigen-binding fragment thereof, glycosylation sites of the antibody can be altered, for example, by mutagenesis (e.g., site-directed mutagenesis). "Glycosylation sites" refer to amino acid residues which are recognized by a eukaryotic cell as locations for the attachment of sugar residues. The amino acids where carbohydrate, such as oligosaccharide, is attached are typically asparagine (N-linkage), serine (O-linkage), and threonine (O-linkage) residues. In order to identify potential glycosylation sites within an antibody or antigen-binding fragment, the sequence of the antibody is examined, for example, by using publicly available databases such as the website provided by the Center for Biological Sequence Analysis for predicting N-linked glycosylation sites and O-linked glycosylation site. Additional methods for altering glycosylation sites of antibodies are described in U.S. Patent Nos. 6,350,861 and 5,714,350.

In yet another embodiment of the invention, antibodies or fragments thereof can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see e.g., Canfield, S. M. and S. L. Morrison (1991) *J. Exp. Med.* 173:1483-1491; and Lund, J. et al. (1991) *J. of Immunol.* 147:2657-2662). Reduction in FcR binding ability of the antibody may also reduce other effector functions which rely on FcR interactions, such as opsonization and phagocytosis and antigen-dependent cellular cytotoxicity.

Uses

The antibodies and labeled antibodies of the present invention may be used in a variety of immunoimaging or immunoassay procedures to detect the presence of cancer in a patient or monitor the status of such cancer in a patient already diagnosed to have it. When used to monitor the status of a cancer, a quantitative immunoassay procedure must be used. If such monitoring assays are carried out periodically and the results compared, a determination may be made regarding whether the patient's tumor burden has increased or decreased. Common assay techniques that may be used include direct and indirect assays. If the sample includes cancer cells, the labeled antibody will bind to those cells. After washing the tissue or cells to remove unbound labeled antibody, the tissue sample is read for the presence of labeled immune complexes. In indirect assays the tissue or cell sample is incubated with unlabeled monoclonal antibody. The sample is then treated with a labeled antibody against the monoclonal antibody (e.g., a labeled antimurine antibody), washed, and read for the presence of ternary complexes.

For diagnostic use the antibodies will typically be distributed in kit form. These kits will typically comprise: the antibody in labeled or unlabeled form in suitable containers, reagents for the incubations for an indirect assay, and substrates or derivatizing agents depending on the nature of the label.

In another embodiment, the antibodies of the present invention have use in treating disease conditions wherein LT-β-R activation is therapeutically beneficial. Such conditions include but are not limited to treating, preventing or reducing the advancement, severity or effects of neoplasia.

In one embodiment of the invention is a method of treating a mammal (i.e. human) for a condition associated with undesired cell proliferation by administering to the mammal a therapeutically effective amount of a composition comprising humanized LT-β-R antibodies of the present invention.

In another embodiment of the invention is a method of treating a mammal (i.e. human) having a solid tumor (i.e. a carcinoma) that overexpresses LT-β-R comprising administering to said mammal a humanized LT-β-R antibody that binds to LT-β-R in an amount effective to reduce the tumor volume. Examples of cancers whose cell proliferation is modulated by LT-β-R may be screened by measuring in vitro the level of LT-β-R and/or LT-β-R ligand (ie LTα1β2 or LIGHT) message expressed in tumor tissue libraries. Tumor tissue libraries in which of LT-β-R and/or LT-β-R ligand (ie LTα1β2 or LIGHT) message is highly expressed would be candidates. Tumor types contemplated in the present invention include solid tumors including but not limited to non small cell lung cancer (NSCLC), colorectal cancer (CRC), breast cancer, as well as on prostate, gastric, skin, stomach, esophagus and bladder cancer.

The humanized antibodies of the subject invention which are used in treating conditions associated with undesired cell proliferation, in particular tumor therapy, advantageously inhibit tumor cell growth, as measured for example by a decrease in the tumor volume, greater than about 10%, 20%, 30% or 40% and most advantageously greater than about 50%. The humanized antibodies are obtained through screening (see, for example, the discussion in Example 10). For example, humanized antibodies for use in the present invention can be selected on the basis of decreased tumor volume versus untreated cancer cells (e.g., greater than about 10%, 20%, 30%, 40% or 50%).

The present invention also provides pharmaceutical compositions comprising a humanized antibody of the present invention and a pharmaceutically acceptable excipient. Suitable carriers, for example, and their formulations, are described in *Remington' Pharmaceutical Sciences*, $16^{th}$ ed., 1980, Mack Publishing Co., edited by Oslo et al. Typically an appropriate amount of a pharmaceutically acceptable salt is used in the formulation to render the formulation isotonic. Examples of the carrier include buffers such as saline, Ringer's solution and dextrose solution. The pH of the solution is preferably from about 5 to about 8, and more preferably from about 7.4 to about 7.8. Further carriers include sustained release preparations such as semipermeable matrices of solid hydrophobic polymers, which matrices are in the form of shaped articles, e.g. liposomes, films or microparticles. It will be apparent to those of skill in the art that certain carriers may be more preferable depending upon, for example the route of administration and concentration of the pharmaceutical composition being administered.

Administration may be accomplished by injection (eg intravenous, intraperitoneal, subcutaneous, intramuscular) or by other methods such as infusion that ensure delivery to the bloodstream in an effective form.

The humanized antibodies of the present invention can be administered at an effective dose to treat the particular clinical condition addressed (i.e. amounts that eliminate or reduce the patient's tumor burden). They will normally be administered parenterally, when possible, at the target cell site, or intravenously. Determination of a preferred pharmaceutical formulation and a therapeutically efficient dose regiment for a given application is well within the skill of the art. The dose and dosage regime will depend upon the nature of the condition (i.e. nature of the cancer), the characteristics of the particular immunotoxin (if used), e.g. its therapeutic index, the patient and the patient's history. An effective dosage is in the range for example of about 0.05 to about 100 milligrams per kilogram of body weight per day. More particularly, about 0.05 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 15 mg, 20 mg, or 25 mg, per kilogram body weight per day. Alternatively about 0.05 to about 100 milligrams, more particularly, about 0.05 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 15 mg, 20 mg, or 25 mg, per kilogram body weight per week. Alternatively about 0.05 to about 100 milligrams, more particularly, about 0.05 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 15 mg, 20 mg, or 25 mg, per kilogram body weight per two weeks. Alternatively about 0.05 to about 100 milligrams, more particularly, about 0.05 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 15 mg, 20 mg, or 25 mg, per kilogram body weight per three weeks. Alternatively about 0.05 to about 100 milligrams, more particularly, about 0.05 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 15 mg, 20 mg, or 25 mg, per kilogram body weight per four weeks.

In another embodiment, tumor cells are treated by 1) administering to a patient humanized antibodies of the present invention and 2) chemotherapeutic agents. Examples of chemotherapeutic agents include but are not limited to cisplatin, taxol, camptosar, adriamycin (dox), 5-FU, gemcitabine, DM-1 (available from Immunogen), vinblastine, actinomycin D, etoposide, methotrexate, and doxorubicin. Several variables will be taken into account by the ordinary artisan in determining a therapeutic regiment and dosages to be administered to an individual, including for example, the administration route and the clinical conditions of the patient. In one embodiment, the antibodies of the invention are designed to be administered in the presence of a chemotherapeutic agent or radiation. In another embodiment, the antibodies of the invention are formulated and packaged with instructions for use in conjunction with chemotherapy or radiation, or marketed or promoted for use in conjunction with chemotherapy or radiation.

Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. See, for example, *Molecular Cloning: A Laboratory Manual*, 2nd edition. (Sambrook, Fritsch and Maniatis, eds.), Cold Spring Harbor Laboratory Press, 1989; *DNA Cloning*, Volumes I and II (D. N. Glover, ed), 1985; *Oligonucleotide Synthesis*, (M. J. Gait, ed.), 1984; U.S. Pat. No. 4,683,195 (Mullis et al.,); *Nucleic Acid Hybridization* (B. D. Hames and S. J. Higgins, eds.), 1984; Transcription and Translation (B. D. Hames and S. J. Higgins, eds.), 1984; *Culture of Animal Cells* (R. I. Freshney, ed). Alan R. Liss, Inc., 1987; *Immobilized Cells and Enzymes*, IRL Press, 1986; *A Practical Guide to Molecular Cloning* (B. Perbal), 1984; *Methods in Enzymology*, Volumes 154 and 155 (Wu et al., eds), Academic Press, New York; *Gene Transfer Vectors for Mammalian Cells* (J. H. Miller and M. P. Calos, eds.), 1987, Cold Spring Harbor Laboratory; *Immunochemical Methods in Cell and Molecular Biology* (Mayer and Walker, eds.), Academic Press, London, 1987; *Handbook of Experiment Immunology*, Volumes I-IV (D. M. Weir and C. C. Blackwell, eds.), 1986; *Manipulating the Mouse Embryo*, Cold Spring Harbor Laboratory Press, 1986.

The following Examples are provided to illustrate the present invention, and should not be construed as limiting thereof.

EXAMPLES

Example 1

Cloning of the muBHA10 Variable Regions

Total cellular RNA from BHA10 murine hybridoma cells (ATCC Accession No. HB-11795) was prepared using the Qiagen RNeasy mini kit following the manufacturer's recommended protocol. cDNAs encoding the variable regions of the heavy and light chains were cloned by reverse transcriptase polymerase chain reaction (RT-PCR) from total cellular RNA using the GIBCO BRL SuperScript Preamplification System for First Strand cDNA Synthesis following the manufacturer's recommended protocol using random hexamers for priming.

The primers used for PCR amplification of the murine BHA10 immunoglobulin heavy chain variable domain were: 5' TGA GGA GAC GGT GAC CGT GGC CCT TGG CCC C 3' (SEQ ID NO: 17) and 5' AGG TSM ARC TGC AGS AGT CWG G 3' (S=C/G, M=A/C, R=A/G, and W=A/T) (SEQ ID NO: 18). The BHA10 light chain variable domain containing the signal sequence was amplified with the following primers: 5' ACT AGT CGA CAT GGG CWT CAA GAT GGA GTC ACA KWY YCW GG 3' (K=G/T, W=A/T, and Y=C/T) (SEQ ID NO: 19) and 5' GTT AGA TCT CCA GCT TGG TCC C 3' (SEQ ID NO: 20). The PCR was subjected to a hot start of 3 minutes at 94° C., then 35 cycles using Clontech's AdvanTaq DNA polymerase: denature 1 minute at 94° C., anneal 1 minute at 50° C., and elongate 2 minutes at 68° C., and then a final 7 minute elongation at 68° C. The PCR products were gel-purified using the Qiagen Qiaquick gel extraction kit following the manufacturer's recommended protocol. Purified BHA10 PCR products were subcloned into Invitrogen's pCR2.1-TOPO cloning vector using their TOPO TA cloning kit following the manufacturer's recommended protocol. The heavy chain RT-PCR subclones were designated pAND138. The light chain RT-PCR subclones were designated pAND145. Inserts from multiple independent subclones were sequenced. With the exception of degenerate positions within PCR primers, the insert sequences of the independent subclones were identical. The N-terminal amino acid sequence for the mature light chain predicted by the cDNA sequence from the PCR product amplified with a signal sequence exactly matched the N-terminal sequence of purified authentic BHA10 light chain derived from Edman degradation (DIVMTQSQKF) (SEQ ID NO: 21). The predicted sequence for the mature heavy chain residues 1-16 matched that determined by Edman degradation of the deblocked purified BHA10 heavy chain ([Q] VQLQQSGPELVKPGA) (SEQ ID NO: 22).

Blast analyses of the variable domain sequences confirmed their immunoglobulin identity. The BHA10 heavy chain variable domain is a member of murine subgroup II(B). Tucker et al. *Science* 206:1299-1303 (1979). The BHA10 light chain variable region is a member of murine kappa subgroup I. Kabat et al. (1991) Sequence of Proteins of Immunological Interest. $5^{th}$ Ed., U.S. Dept Health and Human Services. The predicted amino acid sequences of the BHA10 murine variable light and heavy domains are shown in SEQ ID NO: 1 and 2, respectively.

Example 2

Construction and Expression of chBHA10 cDNAs encoding the murine BHA10 variable regions of the heavy and light chains were used to construct vectors for expression of murine-human chimeras (chBHA10) in which the muBHA10 variable regions were linked to human IgG1 (Ellison et al. (1982) Nucleic Acids Res. 10:4071-4079) and kappa constant regions (Heiter et al. (1980) Cell 22:197-207). For construction of the heavy chain chimera, a 0.32 kb partial PstI-BstEII fragment from the BHA10 heavy chain subclone pAND138 was subcloned into the dephosphorylated 2.82 kb PstI-BstEII vector fragment from the 5a8 heavy chain plasmid pLCB7 (5a8 is a molecularly cloned CD4-specific mAb-ATCC Accession No. HB-10881)), to add a murine heavy chain signal sequence at the 5' end and a splice donor site to the 3' end of the muBHA10 heavy chain variable region. In this plasmid, called pAND146, the heavy chain mature N-terminus is reconstituted to match the N-terminal sequence of purified authentic BHA10 heavy chain (QVQLQQSGP) (SEQ ID NO: 23). The heavy chain sequence in the resultant plasmid pAND146 was confirmed by DNA sequencing. The 0.43 kb NotI-HindIII heavy chain variable domain fragment from pAND146 and the 1.21 kb HindIII-NotI fragment from the plasmid pEAG964, containing a human IgG1 constant region, were subcloned into the NotI site of the pCEP4 (Invitrogen) EBV expression vector-derived plasmid pCH269, producing plasmid pAND147.

For construction of the light chain chimera, a 0.42 kb EcoRI fragment from the BHA10 light chain variable domain plasmid pAND145 was subcloned into the EcoRI site of the linearized, phosphatased pUC-derived cloning vector pNN09. This step added flanking NotI sites in the resulting plasmid, pAND149. The light chain sequence in plasmid pAND149 was confirmed by DNA sequencing. The 0.45 kb NotI-BglII light chain variable domain fragment from pAND149 and the 0.68 kb BclI-NotI fragment from the plasmid pEAG963, containing a human kappa light chain constant domain, were subcloned into the NotI site of the pCEP4 (Invitrogen) EBV expression vector-derived plasmid pCH269, producing plasmid pAND 151.

Expression vectors (chBHA10 heavy chain vector pAND147 and chBHA10 light chain vector pAND151) were co-transfected into 293-EBNA cells, and transfected cells were tested for antibody secretion and specificity. Empty vector-transfected cells, or cells co-transfected with EBV expression vectors for hu5c8 (a molecularly cloned CD154-specific mAb), and huCBE11 (an LT-β-R-specific mAb (the cell line of which has been assigned the ATCC patent deposit designation PTA-3357)) served as controls. Western blot analysis (developed with anti-human heavy and light chain antibodies) of protein A immunoprecipitates from whole cell lysates and conditioned medium indicated that chBHA10-transfected cells synthesized and efficiently secreted antibody heavy and light chains at levels similar to hu5c8- or huCBE11-transfected cells. FACS analysis of LT-β-R-expressing HT-29 cells stained with conditioned medium from transfected cells indicated that the chBHA10 antibody bound and produced staining patterns similar to those of muBHA10 and huCBE11, while conditioned medium from mock- and hu5c8-transfected cells failed to stain LT-β-R on HT-29 cells. Chimeric BHA10 produced from a large-scale transient transfection was purified and demonstrated to stain LT-β-R on HT-29 cells with an apparent Kd about two-fold higher than that of huCBE11, consistent with the relative affinities measured for muCBE11 and muBHA10 (Browning et al., *J. Exp. Med.* 183:867, 1996).

Example 3

Construction of Reshaped BHA10 Variable Domains

The BHA10 light chain variable domain corresponds to human kappa I (Hieter et al. (1980) *Cell* 22:197-207) and the heavy chain variable domain corresponds to human heavy subgroup I (Ellison et al. (1982) *Nucleic Acids Res.* 10:4071-4079). The choice of the human acceptor frameworks was by homology matching to human germline sequences using the program IgBLAST. Sato et al. *Mol. Immunol.* 31:371-381 (1994): human L1/L15/J1 (Bentley et al. (1983) *Cell* 32:181-189; Cox et al. (1994) *Eur. J. Immunol.*, 24:827-836 and Heiter et al. (1982) *J. Biol. Chem.* 257:1516-1522) for the light chain, and human 1-69/J6 (Tomlinson et al. (1992) *J. Mol. Biol.*, 227:776-798 and Mattila et al. (1995) *Eur. J. Immunol.*, 25:2578-2582) for the heavy chain. Three versions of each of the variable light and variable heavy reshaped chains were designed. In general the first version contains the most back mutations to the murine donor sequences, while the third version contains the fewest (i.e., the most "humanized").

The BHA10 variable regions were made by a combination of unique site elimination (USE) and Quikchange mutagenesis using Clontech's Transformer mutagenesis and Stratagene's Quikchange mutagenesis kits and following the manufacturers' recommended protocols. The chBHA10 variable domain plasmids pAND146 and pAND149 were used as starting templates. The mutagenic primers for the framework (FR) changes are described below. The cDNA sequences of the human acceptor frameworks were used, with silent mutations introduced to produce restriction site changes to facilitate identification of mutated plasmids. Mutated plasmids were identified by screening for the introduced restriction site changes. The variable region cDNA sequences in the resultant plasmids were confirmed by DNA sequencing.

The various BHA10 based plasmids and corresponding expression vectors described below are listed in Table 2.

Reshaped Variable Heavy Chains (VH)

Variable heavy chain, version 1, was initially mutated by USE mutagenesis using pAND146 template with framework 2 (FR2) primer 5' GCA CTG GGT GAG GCA GGC CCC TGG ACA GGG ACT TG 3' (SEQ ID NO: 24) deleting a StuI restriction site and creating plasmid pKJS030. That plasmid was subsequently subjected to two rounds of Quikchange mutagenesis with oligo pairs 5' CCC AGG TCC AAC TGG TGC AGT CTG GAG CTG AGG 3' (SEQ ID NO: 25) and its complement for framework 1 (FR1) and 5' GAA GTT CAA GGG CAG GGC CAC ACT GAC AGC AGA CAA ATC CAC CAG CAC AGC CTA CAT GGA GCT CAG CAG CCT GAG GTC TGA AGA TAC TGC GGT CTA TTT CTG TGC AAG ATC C 3' (SEQ ID NO: 26) and its complement for framework 3 (FR3), with each pair deleting a PstI site. The resultant reshaped variable heavy chain (VH#1) plasmid was designated pKJS036.

Variable heavy chain, version 2, used pAND146 template which was subjected to a single round of USE mutagenesis with framework 1 primer 5' CAG GTC CAA CTG GTG CAG TCT GGA GCT GAG GTG AAG AAG CCT GGG TCC TCA GTG AAG GTG TCC TGC AAG GC 3' (SEQ ID NO: 27) deleting EcoRV and PstI sites; framework 2 primer 5' GCA CTG GGT GAG GCA GGC CCC TGG ACA GGG ACT TG 3' (SEQ ID NO: 28) deleting a StuI site; and framework 3 primer 5' GAA GTT CAA GGG CAG GGC CAC AAT CAC TGC AGA CAA ATC CAC CAG CAC AGC CTA CAT GGA GCT CAG CAG CCT GAG GTC TGA AGA TAC TGC GGT CTA TTA CTG TGC AAG ATC C 3' (SEQ ID NO: 29) generating a SacI site. The resultant reshaped variable heavy chain (VH#2) plasmid was designated pKJS031.

Variable heavy chain, version 3, was initially mutated by USE mutagenesis using pAND146 template with framework 1 primer 5' CAG GTC CAA CTG GTG CAG TCT GGA GCT GAG GTG AAG AAG CCT GGG TCC TCA GTG AAG GTG TCC TGC AAG GC 3' (SEQ ID NO: 30) which deleted EcoRV and PstI sites and framework 3 primer 5' GAA GTT CAA GGG CAG GGT CAC AAT CAC TGC AGA CAA ATC CAC CAG CAC AGC CTA CAT GGA GCT CAG CAG CCT GAG GTC TGA AGA TAC TGC GGT CTA TTA CTG TGC AAG ATC C 3' (SEQ ID NO: 31) which generated a SacI site, creating plasmid pKJS032. Plasmid pKJS032 was then used as a template for Quikchange mutagenesis with the framework 2 primer pair 5' GGC CCC TGG ACA GGG ACT TGA GTG GAT GGG ATG GAT TTA TCC TGG 3' (SEQ ID NO: 32) and its complement resulting in the loss of a HpaII site. The resultant reshaped variable heavy chain (VH#3) plasmid was designated pKJS037.

Expression vectors for the huBHA10 heavy chains were made by subcloning the 0.425 kb NotI-HindIII heavy chain variable domain fragments from pKJS036, pKJS031, or pKJS037, and the 1.21 kb HindIII-NotI fragment from the plasmid pEAG964, containing a human IgG1 constant region, into the NotI site of the pCEP4 EBV expression vector-derived plasmid pCH274, producing heavy chain expression vectors pKJS044 (heavy chain #1 expression vector), pKJS045 (heavy chain #2 expression vector), and pKJS046 (heavy chain #3 expression vector).

Reshaped Variable Light Chain (VL)

Variable light chain, version 1, initially underwent USE mutagenesis on template plasmid pAND149 with framework 1 primer 5' GAT GGA GAC ATT CAG ATG ACC CAG TCT CCT AGC TCC CTG TCC GCC TCA GTA GGA GAC AGG GTC ACC ATC ACC TGC AAG GC 3' (SEQ ID NO: 33), the framework 2 primer 5' GTA GCC TGG TTC CAA CAG AAA CCC GGG AAG GCT CCT AAA TCA C 3' (SEQ ID NO: 34) which introduced an XmaI site, the 5' framework 3 primer 5' CAG TGG AGT CCC TTC TAG ATT CAC AGG CAG 3' (SEQ ID NO: 35) which introduced a XbaI site, and the 3' framework 3 primer 5' CTC ACC ATC AGC AGC CTG CAG CCT GAA GAC TTC GCA ACC TAT TTC TGT CAG C 3' (SEQ ID NO: 36) which introduced a PstI site. The resultant plasmid was designated pKJS033. Plasmid pKJS033 contained undesirable residues within framework 2 and was therefore subjected to Quikchange mutagenesis using a second framework 2 primer pair 5' GGG TAT TAA TGT AGC CTG GTA TCA ACA GAA ACC AGG GAA GGC TCC 3' (SEQ ID NO: 37) and its complement, which removed the XmaI site and added a BclI site. Plasmid pKJS033 also underwent an additional round of Quikchange mutagenesis with the framework 4 primer pair 5' CCT ATC CAT TCA CGT TCG GCC AGG GTA CCA AGG TGG AGA TCT AAC AAG GGC G 3' (SEQ ID NO: 38) and its complement, introducing a unique KpnI site. These reactions generated plasmid pKJS038. Plasmid pKJS038 contained errors within framework 2 and was therefore subjected to an additional round of Quikchange mutagenesis with a third framework 2 primer pair, 5' CCC TGG TTT CTG TTG ATA CCA GGC AAC GTT AAT ACC CAC 3' (SEQ ID NO: 39) and its complement, resulting in the loss of the BclI site. The resultant reshaped variable light chain (VL#1) plasmid was designated pKJS051.

Variable light chain version 2 initially underwent USE mutagenesis on template Plasmid pAND149 with the framework 1 primer 5' GAT GGA GAC ATT CAG ATG ACC CAG TCT CCT AGC TCC CTG TCC GCC TCA GTA GGA GAC AGG GTC ACC ATC ACC TGC AAG GC 3' (SEQ ID NO: 40), the framework 2 primer 5' GTA GCC TGG TTC CAA CAG AAA CCC GGG AAG GCT CCT AAA TCA C 3' (SEQ ID NO: 41) which added an XmaI site, with the 5' framework 3 primer 5' CAG TGG AGT CCC TTC TAG ATT CAG CGG CAG TGG ATC 3' (SEQ ID NO: 42) which added an XbaI site, and with the 3' framework 3 primer 5'CTC ACC ATC AGC AGC CTG CAG CCT GAA GAC TTC GCA ACC TAT TTC TGT CAG C 3' (SEQ ID NO: 43) which added a PstI site. The resultant plasmid was designated pKJS034. Plasmid pKJS034 contained undesirable mutations within both framework 3 and framework 2. The framework 3 mutations were corrected in plasmid pKJS034 by successive rounds of Quikchange mutagenesis using the new 3' framework 3 primer pair 5' GCT GAC AGA AAT AGG TTG CGA AGT CTT CAG GCT GGA GGC TGC TGA TGG 3' (SEQ ID NO: 44) and its complement, which removed the PstI site; and the new 5' framework 3 primer 5' GGT ACA GTG GAG TCC CTT CCA GAT TCA GCG GCA GTG GAT CTG GG 3' (SEQ ID NO: 45) and its complement, which removed the XbaI site. Framework 2 errors on pKJS034 were then corrected by another round of mutagenesis with the primer pair 5' GGG TAT TAA TGT AGC CTG GTA TCA ACA GAA ACC AGG GAA GGC TCC 3' (SEQ ID NO: 46) and its complement, which removed the XmaI site and added a BclI site. Plasmid pKJS034 was then subjected to a final round of Quikchange mutagenesis with the framework 4 primer pair 5' CCT ATC CAT TCA CGT TCG GCC AGG GTA CCA AGG TGG AGA TCT AAC AAG GGC G 3' (SEQ ID NO: 47) and its complement, which introduced a KpnI site. The resultant reshaped variable light chain (VL#2) plasmid was designated pKJS039.

Variable light chain version 3 initially underwent USE mutagenesis on template plasmid pAND149 with the framework 1 primer 5' GAT GGA GAC ATT CAG ATG ACC CAG TCT CCT AGC TCC CTG TCC GCC TCA GTA GGA GAC AGG GTC ACC ATC ACC TGC AAG GC 3' (SEQ ID NO: 48), the framework 2 primer 5' GTA GCC TGG TTC CAA CAG AAA CCC GGG AAG GCT CCT AAA TCA C 3' (SEQ ID NO: 49) incorporating an XmaI site, the 5' framework 3 primer 5' CAG TGG AGT CCC TTC TAG ATT CAG CGG CAG TGG ATC 3' (SEQ ID NO: 50) incorporating an XbaI site, and the 3' framework 3 primer 5' CTC ACC ATC AGC AGC CTG CAG CCT GAA GAC TTC GCA ACC TAT TAC TGT CAG CAA TAT G 3' (SEQ ID NO: 51) incorporating a Pst I site, generating pKJS035. Plasmid pKJS035 underwent a single round of Quikchange mutagenesis with the framework 4 primer pair 5' CCT ATC CAT TCA CGT TCG GCC AGG GTA CCA AGG TGG AGA TCT AAC AAG GGC G 3' (SEQ ID NO: 52) and its complement, incorporating a new KpnI site. The resultant reshaped variable light chain (VL#3) plasmid was designated pKJS040.

Expression vectors for the huBHA10 light chains were made by subcloning the 0.453 kb NotI-BglII light chain variable domain fragments from pKJS051, pKJS039, or pKJS040 and the 0.678 kb BclI-NotI fragment from the plasmid pEAG963, containing a human kappa light chain constant domain into the NotI site of the pCEP4 EBV expression vector-derived plasmid pCH274, producing light chain expression vectors pKJS048 (light chain #1 expression vector), pKJS049 (light chain #2 expression vector), and pKJS050 (light chain #3 expression vector).

Example 4

Construction and Expression of Reshaped Humanized BHA10 Antibodies (Versions 1, 2, 3 and 4)

Figure 2:
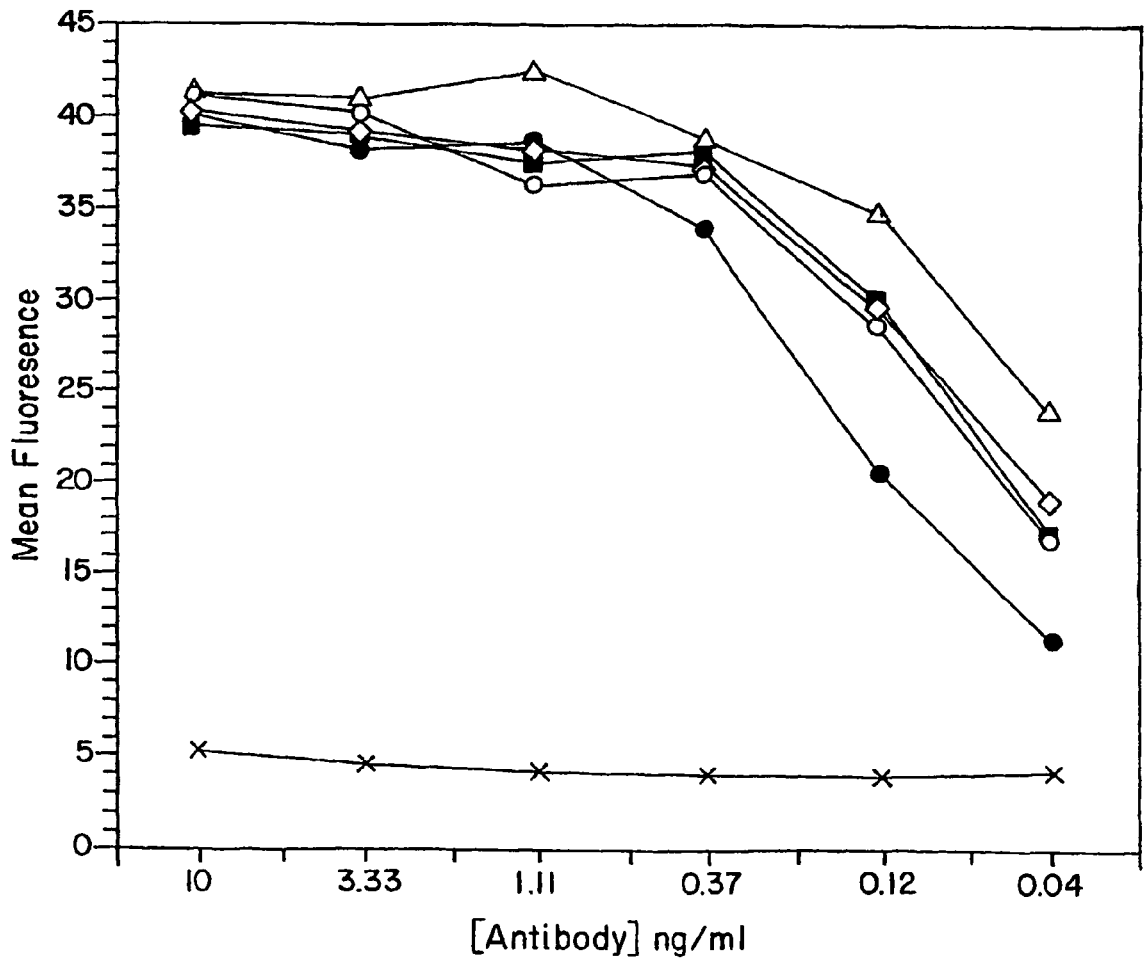
FIG. 2 shows the results of FACS analysis of purified huBHA10 antibody Versions 2-4 binding to HT29 cells. FACS analysis was carried out as in Example 8. Closed square: chimeric BHA10; open circle: Version 2; closed circles: Version 3; open diamond: Version 4; open triangle: huCBE11 (positive control); crosses: M92 (anti-CD40L antibody) (negative control).
Figure 3:
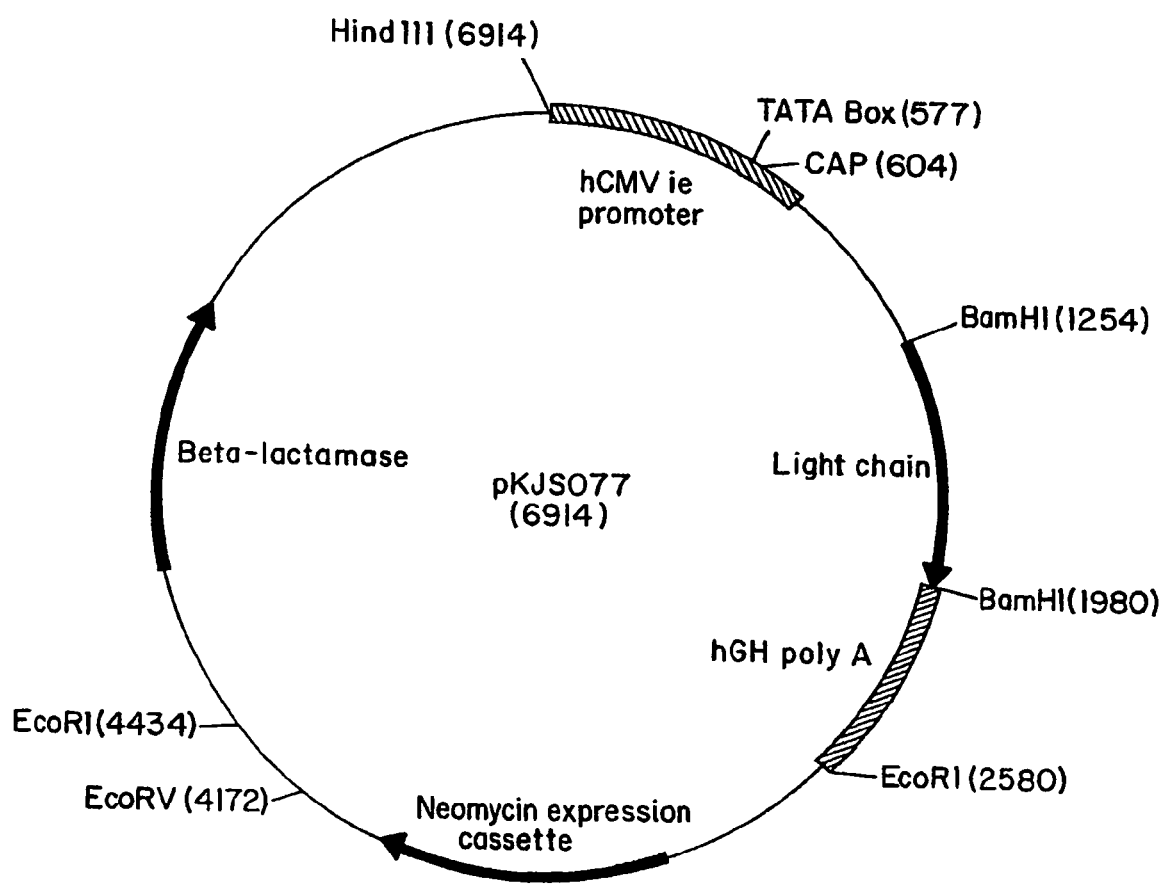
FIG. 3 illustrates the plasmid map of pKJS077. This plasmid contains Light Chain #2 and neomycin resistance genes. The light chain expression cassette contains the human CMV immediate early promoter and first intron (containing a small deletion) as well as the human growth hormone polyadenylation sequence.

The various expression vectors described above were paired together and are listed and described in Table 2 and were co-transfected into 293-EBNA cells. Version 1 huBHA10 comprised the pairing of pKJS44 (heavy chain #1 expression vector) and pKJS48 (light chain #1 expression vector); Version 2 huBHA10 comprised the pairing of pKJS45 (heavy chain #2 expression vector) and pKJS49 (light chain #2 expression vector); Version 3 huBHA10 comprised the pairing of pKJS46 (heavy chain #3 expression vector) and pKJS50 (light chain #3 expression vector); and Version 4 huBHA10 comprised the pairing of pKJS46 (heavy chain #3 expression vector) and pKJS49 (light chain #2 expression vector). The vectors were co-transfected into 293-EBNA cells and these transfected cells were tested for antibody secretion and specificity. Western blot analysis (detection with anti-human heavy and light chain antibodies) of conditioned medium indicated that huBHA10-transfected cells synthesized and efficiently secreted heavy and light chains at levels similar to chBHA10-transfected cells. FACS analysis of LT-β-R-expressing HT-29 cells stained with conditioned medium from transfected cells indicated that the Version 3 huBHA10 mAb bound less well than Version 2 huBHA10 which was similar to chBHA10 (FIG. 3). Mix and match co-transfections suggested that the reduction could be attributed to the variable light chain (VL#3) of Version 3 (FIG. 2), which differed from Version 2's variable light chain (VL#2) at two framework residues: residues 36 and 87. Version 4 huBHA10 was then constructed by pairing pKJS46 (heavy chain #3 expression vector) and pKJS49 (light chain #2 expression vector).

Co-transfections of 293-EBNA cells with chBHA10 and huBHA10 Versions 1-4 were scaled up and conditioned medium was harvested. Antibody was purified on Protein A-Sepharose and purified mAbs were assayed for activity. Binding to the lymphotoxin-beta receptor was determined by FACS analysis of protein A-purified antibodies on the cell-line HT29.

Example 5

IL-8—Agonism on A375 Cells

A375 cells were plated at $10^5$/ml into 96-well plates containing either soluble antibodies or antibodies captured onto goat anti-human IgG Fc (Jackson ImmunoResearch Laboratories)-coated wells. The culture plates were incubated overnight. Protein-A purified antibodies from 293-E cells transfected with BHA10 variants were assayed at the indicated concentrations shown in FIG. 1. Protein A purified hu-CBE11 was used as a positive control. IL-8 agonism on A375 cells is shown in FIG. 1. Rank ordering of bioactivity was chBHA10=Version 4 huBHA10=Version 2 huBHA10>Version 3 huBHA10. Because Version 4 huBHA10 was more humanized than Version 2 huBHA10, it was selected for the generation of a stable CHO cell line.

Example 6

Construction of Stable CHO Expression Vectors for Version 4 huBHA10

EBV expression vectors for huBHA10 Version 4 (light chain #2 expression vector: pKJS049; heavy chain #3 expression vector: pKJS046) were co-transfected into 293-EBNA cells and transfected cells were tested for antibody secretion. Western blot analysis of conditioned medium confirmed that transfected cells synthesized and efficiently secreted heavy and light chains. The EBV vectors contain extraneous 5' and 3' UTRs and an intron separating the immunoglobulin variable domain and the constant domain, whereas cDNA is desired for the stable CHO expression vector(s). Therefore, the cDNAs were cloned by RT-PCR.

Total cellular RNA from transiently-co-transfected huBHA10-expressing cells was prepared using a Qiagen RNeasy mini kit following the manufacturer's recommended protocol. cDNAs encoding the heavy and light chains were cloned by RT-PCR from total cellular RNA using the Amersham-Pharmacia First Strand cDNA Synthesis kit following the manufacturer's recommended protocol using 5' CGG ATC CTC AAC CGG GAG ACA GGG AGA GGC T 3' (SEQ ID NO: 53) for priming the heavy chain and 5' CGG ATC CCT AAC ACT CTC CCC TGT TGA A 3' (SEQ ID NO: 54) for priming the light chain. For PCR amplification of the huBHA10 immunoglobulin heavy chain cDNA, the primers used were: 5' GCT AGC GGA TCC ACC ATG GAC TGG ACC TGG 3' (SEQ ID NO: 55) (to add a BamHI site and an ACC immediately 5' of the initiator methionine, to add a Kozak signal) and 5' CGG ATC CTC AAC CGG GAG ACA GGG AGA GGC T 3' (SEQ ID NO: 56) (to genetically remove the heavy chain C-terminal lysine residue and add a BamHI site immediately 3' of the termination codon). For PCR amplification of the huBHA10 immunoglobulin light chain cDNA, the primers used were: 5' CCC TTA GGA TCC ACC ATG GGC TTC AAG ATG GAG 3' (SEQ ID NO: 57) (to add a BamHI site and ACC immediately 5' of the initiator methionine, to add a Kozak signal) and 5' CGG ATC CCT AAC ACT CTC CCC TGT TGA A 3' (SEQ ID NO: 58) (to add a BamHI site immediately 3' of the termination codon). The cDNA was subjected to a hot start PCR of 2.5 minutes at 95° C.; 10 cycles using Advantage Taq DNA polymerase (Clontech): denature 0.5 minute at 94° C., anneal 0.75 minute at 55° C., elongate 1 minute at 68° C.; and then a final 5 minute elongation at 68° C. A second amplification using 10 µl from the initial reaction as a sample and Pfu DNA polymerase (Stratagene) was performed: denature 0.5 minute at 94° C., anneal 0.75 minute at 50° C., and elongate 1 minute at 72° C.; and then a final 10 minute elongation at 72° C. The PCR products were gel-purified using a Qiagen Qiaquick gel extraction kit following the manufacture's recommended protocol. Purified PCR products were subcloned into Invitrogen's pCR4TOPO cloning vector following the manufacturer's recommended protocol. Purified PCR products were subcloned into Invitrogen's pCR4TOPO cloning vector following the manufacturer's recommended protocol for TOPO cloning. Inserts from multiple independent subclones were sequenced. The sequence-confirmed light chain cDNA subclone was designated pKJS072. The sequence confirmed heavy chain cDNA subclone was designated pKJS071.

The 726 bp BamHI light chain cDNA fragment from pKJS072 was subcloned into the phosphatased 6.19 kb BamHI vector fragment from the hu5c8 light chain expression vector pXLC2 to make the neo-containing huBHA10 light chain expression pKJS077 (FIG. 3). This plasmid contains the BHA10 version 4 light chain and neomycin resistance genes. The light chain expression cassette contains the human CMV immediate early promoter and first intron (containing a small deletion) as well as the human growth hormone polyadenylation sequence.

Figure 5:
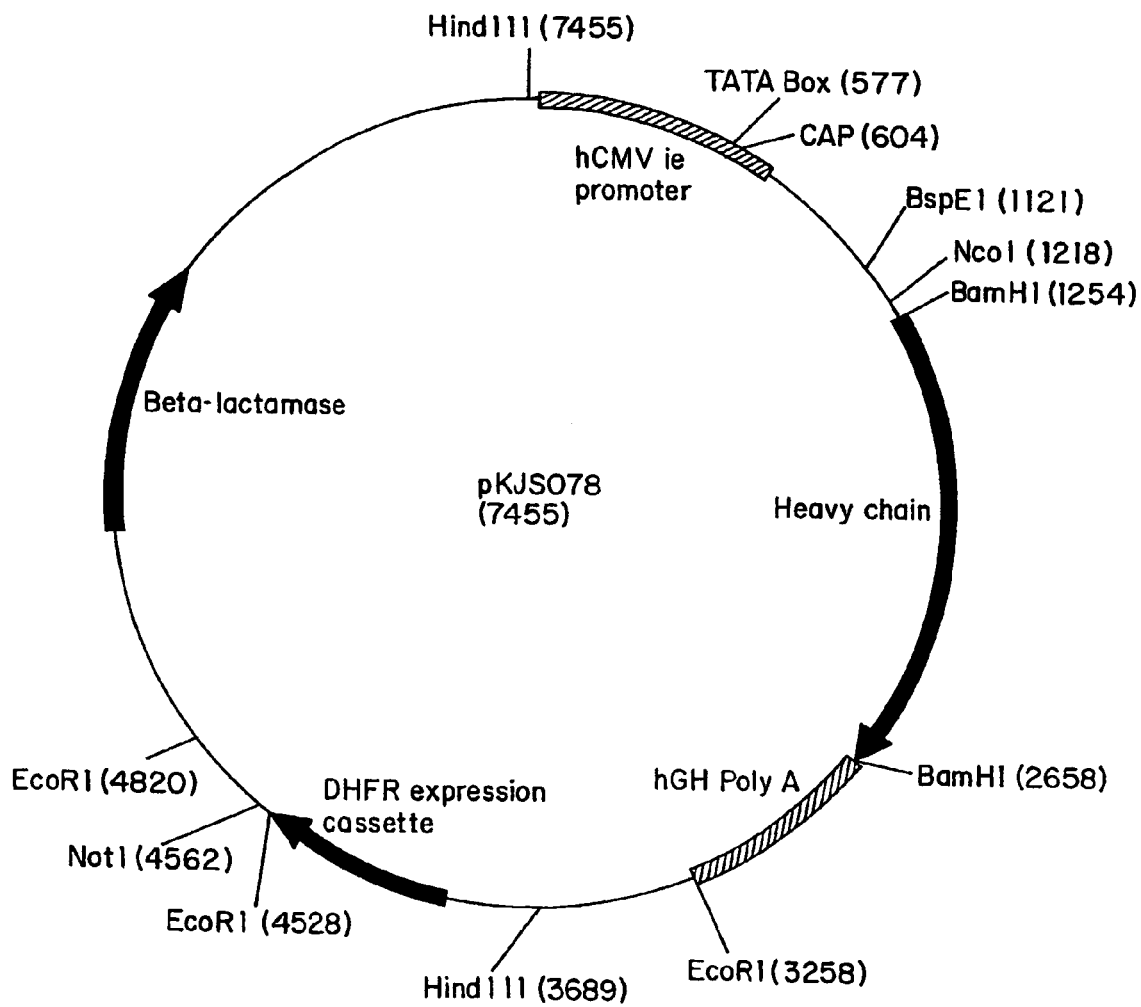
FIG. 5 illustrates the plasmid map of pKJS078. This plasmid contains the Heavy Chain #3 and DHFR genes. The heavy chain expression cassette contains the human CMV immediate early promoter and first intron (containing a small deletion) as well as the human growth hormone polyadenylation sequence. The DHFR expression cassette contains the SV40 early promoter and SV40 polyadenylation sequence.

Similarly, the 1404 bp BamHI heavy chain cDNA fragment from pKJS071 was subcloned into phosphatased BamHI-linearized pV80 to make the dhfr-containing huBHA10 heavy chain vector pKJS078 (FIG. 5). This plasmid contains the BHA10 version 4 heavy chain and dhfr genes. The heavy chain expression cassette contains the human CMV immediate early promoter and first intron (containing a small deletion) as well as the human growth hormone polyadenylation sequence. The dhfr expression cassette contains the SV40 early promoter and SV40 polyadenylation sequence.

Expression vectors were co-transfected into COS cells and transfected cells were tested for antibody secretion and specificity (empty vectors or M92 vectors served as negative controls). Western blot analysis (developed with anti-human heavy and light chain antibodies) of conditioned medium indicated that transfected cells synthesized and efficiently secreted heavy and light chains and in FACS analysis conditioned medium from huBHA10-transfected cells specifically stained LT-β-R-expressing HT-29 cells.

Example 7

CHO Cell Lines Expressing Version 4 huBHA10

Expression plasmids pKJS077 and pKJS078 for Version 4 huBHA10 were transfected into CHO cells.

Example 8

Antibody Affinity Measurement

HT29 cells were harvested by treatment with PBS containing 5 mM EDTA for 30 minutes followed by vigorous agitation. Cells were distributed to round-bottom 96-well plates at $2.5 \times 10^5$ cells/well. Supernatants from 293-E cells transfected with BHA10 variants were added to the wells at the indicated dilutions in a total volume of 100 µl and incubated at 4° C. for 1 hour. The cells were washed twice with FACS buffer (PBS containing 5% FBS) and incubated with a 1:100 dilution of PE-conjugated anti-human heavy and light chain antibody (Jackson ImmunoResearch Laboratories) for 1 hour. The cells were then washed 3 times with FACS buffer and resuspended in 100 µl of PBS containing 1.0% paraformaldehyde. Samples were then transferred to the FACS facility for analysis. Protein A-purified antibodies from 293-E cells transfected with BHA10 variants were assayed at the indicated concentrations as shown in FIG. 2. The Protein A-purified CBE11 and 5C8 (anti-CD40L antibody) research standards were used as positive and negative controls, respectively. Rank ordering of binding activity was chBHA10=Version 4 huBHA10=Version 2 huBHA10>Version 3 huBHA10.

Example 9

Cytotoxicity on WiDr Cells

A cytotoxicity assay using WiDr colon cancer cells with soluble anti-LT-β-R antibodies on anti-human IgG Fc-coated wells demonstrate that the anti-LT-β-R antibodies of the invention increase cytotoxicity in cancer cells. WiDr cells are plated at $6 \times 10^4$/ml in the presence of 80 units/ml huIFN-gamma into 96 well plates containing either soluble antibodies or antibodies captured onto goat anti-human IgG Fc (Jackson ImmunoResearch Laboratories)-coated wells. The culture plates are incubated for 5 days. MTT is added for 4 hrs and the resulting precipitate is dissolved by overnight incubation with 10% SDS in 10 mM HCl, and ODs are read on a microplate reader.

Example 10 huBHA10 Pretreatment Slows Growth of WiDr Tumors 6-week-old nude mice are injected intraperitoneally with 100 ug of anti-LFA3 antibody (1E6), 100 ug anti-LT-β-R antibody (i.e. reshaped huBHA10), or not injected (control). The animals are then injected subcutaneously with $1 \times 10^6$ WiDr colon adenocarcinoma cells. The reshaped huBHA10-treated mice are retreated weekly with 100 ug of antibody and the mBHA10 animals are retreated on day 14 only. Tumor size is measured weekly and the volume of the tumor sphere calculated. Animals are sacrificed when their tumors reach a volume of 2.0 cm³ (16 mm diameter), and their death is noted on a survival chart. Pretreatment with reshaped huBHA10 is expected to slow the progression of the WiDr tumors in nude mice.

Example 11

Slowing Growth of Pregrown WiDr Tumors and Increasing Survival in WiDr Tumor-Bearing Nude Mice $10^6$ WiDr cells are pregrown subcutaneously for 10 days in nude mice. The mice receive subcutaneous injections of either PBS or reshaped huBHA10 weekly or mBHA10 alternate weeks. Tumor weights are calculated from width and length measurements, and animals with tumors over 2000 mg are sacrificed, their tumor weights at time of sacrifice continued into the statistical averaging. Tumor weights are calculated using the formula: (Width×Width×Length)/2=tumor weight in mg. It is expected that the reshaped huBHA10 antibodies of the present invention will slow the progression of pre-grown tumors in vivo. In addition, tumors are grown and treated as described above and percent survival of the animals is measured. It is expected that the reshaped huBHA10 antibodies of the present invention will induce prolonged survival in vivo in mice with pregrown tumors.

TABLE 2

| | Description |
|---|---|
| VH#1 (pKJS036) | Variable heavy chain-version 1 (comprising back mutations Y27, T30, I48, A67, L69 and F91) |
| VH#2 (pKJS031) | Variable heavy chain-version 2 (comprising back mutations Y27, T30, I48 and A67) |
| VH#3 (pKJS037) | Variable heavy chain-version 3 (comprising back mutations Y27 and T30) |
| VL#1 (pKJS051) | Variable light chain-version 1 (comprising back mutations Y36, S49, T63 and F87) |
| VL#2 (pKJS039) | Variable light chain-version 2 (comprising back mutations Y36, S49 and F87) |
| VL#3 (pKJS040) | Variable light chain-version 3 (comprising back mutations S49) |
| Heavy chain #1 (pKJS044) | Heavy chain-version 1 (comprising VH#1 and heavy constant chain human IgG1) |
| Heavy chain #2 (pKJS045) | Heavy chain-version 2 (comprising VH#2 and heavy constant chain human IgG1) |
| Heavy chain #3 (pKJS046) | Heavy chain-version 3 (comprising VH#3 and heavy constant chain human IgG1) |
| Light chain #1 (pKJS048) | Light chain-version 1 (comprising VL#1 and light constant chain human kappa) |
| Light chain #2 (pKJS049) | Light chain-version 2 (comprising VL#2 and light constant chain human kappa) |
| Light chain #3 (pKJS050) | Light chain-version 3 (comprising VL#3 and light constant chain human kappa) |
| Version 1 huBHA10 | Version 1 huBHA10 comprising Heavy chain #1 and Light chain #1 |
| Version 2 huBHA10 | Version 2 huBHA10 comprising Heavy chain #2 and Light chain #2 |
| Version 3 huBHA10 | Version 3 huBHA10 comprising Heavy chain #3 and Light chain #3 |
| Version 4 huBHA10 | Version 4 huBHA10 comprising Heavy chain #3 and Light chain #2 |
| pKJS077 | Light chain #2 |
| pKJS078 | Heavy chain #3 |

It will be apparent to those skilled in the art that various modifications and variations can be made in the polypeptides, compositions and methods of the invention without departing from the spirit or scope of the invention. Thus, it is intended that the present invention cover the modifications and variations of this invention provided that they come within the scope of the appended claims and their equivalents. All publications and patent documents cited herein, as well as text appearing in the figures and sequence listing, are hereby incorporated by reference in their entirety for all purposes to the same extent as if each were so individually denoted.

What is claimed is:

1. A humanized anti-lymphotoxin-beta receptor (LT-β-R) antibody, or antigen-binding fragment thereof, comprising
a light chain comprising the complementary determining regions set forth in SEQ ID NO:1, and residue S49 (Kabat numbering convention), and, optionally, at least one of the following residues Y36, T63 and F87 (Kabat numbering convention), wherein the remainder of the light chain is from a human acceptor framework, and
a heavy chain variable domain sequence set forth in SEQ ID NO: 14.

2. A humanized anti-lymphotoxin-beta receptor (LT-β-R) antibody, or antigen-binding fragment thereof, comprising
a light chain variable domain sequence set forth in SEQ ID NO: 6, and
a heavy chain comprising the complementary determining regions set forth in SEQ ID NO: 2 and residues Y27 and T30 (Kabat numbering convention), and, optionally, at least one of the following residues: I48, A67, L69, or F91 (Kabat numbering convention), wherein the remainder of the heavy chain is from a human acceptor framework.

3. A humanized antibody, or antigen-binding fragment thereof, which specifically binds LT-β-R, comprising a light chain comprising SEQ ID NO: 15, and a heavy chain comprising SEQ ID NO: 16.

4. The humanized antibody of claim 1, wherein the antibody comprises a light chain variable domain sequence set forth in SEQ ID NO:6.

5. The humanized antibody of claim 2, wherein the antibody comprises a heavy chain variable domain sequence set forth in SEQ ID NO:14.

6. The humanized antibody of claim 1 or 2, wherein the antibody comprises the light chain sequence set forth in SEQ ID NO:15.

7. The humanized antibody of claim 1 or 2, wherein the antibody comprises the heavy chain sequence set forth in SEQ ID NO:16.

8. The humanized antibody according to any one of claims 1, 2, or 3, wherein the antibody is further linked to a cytotoxic moiety or a chemotherapeutic drug.

9. A pharmaceutical composition comprising the humanized antibody according to any one of claims 1, 2, or 3, and a pharmaceutically acceptable carrier.

10. The humanized antibody according to any one of claims 1, 2, or 3, wherein the fragment is selected from the group consisting of a Fab fragment, a Fab' fragment, a F(ab)₂ fragment, and a F_v fragment.

11. The humanized antibody or antigen-binding fragment according to any one of claims 1, 2, or 3, wherein the antibody comprises a modification selected from the group consisting of
a) the antibody is conjugated to polyethylene glycol or albumen;
b) the constant region of the antibody is modified to reduce at least one constant region-mediated biological effector function relative to an unmodified antibody; and
c) the antibody comprises a Fc region having an altered effector function.

12. The humanized antibody or antigen-binding fragment according to any one of claims 1, 2, or 3, wherein the antibody is an IgG1.

13. An antibody, or an antigen-binding fragment thereof, comprising the same heavy and light variable chain polypeptide sequences as an antibody produced by cell line 3D9 (ATCC Accession No. PTA-4726).

14. An isolated hybridoma deposited with the ATCC as Accession No. PTA-4726.

15. A humanized anti-lymphotoxin-beta receptor (LT-β-R) antibody, or antigen-binding fragment thereof, comprising a) a light chain consisting of
  i) complementary determining regions (CDRs) as set forth in SEQ ID NO: 1,
  ii) a framework region from a human acceptor framework, and
  iii) framework residues Y36, S49, and F87 (Kabat numbering convention), and
b) a heavy chain variable domain sequence as set forth in SEQ ID NO: 14.

16. A humanized anti-lymphotoxin-beta receptor (LT-β-R) antibody, or antigen-binding fragment thereof, comprising
  a) a light chain variable domain sequence as set forth in SEQ ID NO: 6; and
  b) a heavy chain consisting of
    i) complementary determining regions (CDRs) as set forth in SEQ ID NO: 2,
    ii) a framework region from a human acceptor framework, and
    iii) framework residues Y27 and T30 (Kabat numbering convention).

17. A humanized anti-lymphotoxin-beta receptor (LT-β-R) antibody, or antigen-binding fragment thereof, comprising
  a light chain variable domain sequence set forth in SEQ ID NO: 6, and
  a heavy chain comprising the complementary determining regions set forth in SEQ ID NO: 2, wherein the antibody comprises at least one of the following residues in its heavy chain: Y27, T30, I48, A67, L69, or F91 (Kabat numbering convention).

18. A humanized anti-lymphotoxin-beta receptor (LT-β-R) antibody, or antigen-binding fragment thereof, comprising
  a heavy chain variable domain sequence set forth in SEQ ID NO: 14, and
  a light chain comprising the complementary determining regions set forth in SEQ ID NO:1, wherein the antibody comprises at least one of the following residues in its light chain: Y36, S49, T63 and F87 (Kabat numbering convention).

19. The humanized antibody according to claim 17 or 18, wherein the antibody is further linked to a cytotoxic moiety or a chemotherapeutic drug.

20. A pharmaceutical composition comprising the humanized antibody according to claim 17, or 18, and a pharmaceutically acceptable carrier.

21. The humanized antibody according to claim 17 or 18, wherein the fragment is selected from the group consisting of a Fab fragment, a Fab' fragment, a F(ab)$_2$ fragment, and a F$_v$ fragment.

22. The humanized antibody or antigen-binding fragment according to claim 17 or 18, wherein the antibody comprises a modification selected from the group consisting of
  a) the antibody is conjugated to polyethylene glycol or albumen;
  b) the constant region of the antibody is modified to reduce at least one constant region-mediated biological effector function relative to an unmodified antibody; and
  c) the antibody comprises a Fc region having an altered effector function.

23. The humanized antibody or antigen-binding fragment according to claim 17 or 18, wherein the antibody is an IgG1.

* * * * *